US012734061B1

(12) United States Patent
Karnezis et al.

(10) Patent No.: US 12,734,061 B1
(45) Date of Patent: Sep. 15, 2026

(54) EXTERNAL NASAL DILATORS

(71) Applicant: ENT INNOVATIONS INC., Redondo Beach, CA (US)

(72) Inventors: Anastasios Karnezis, Redondo Beach, CA (US); Shawn Iravanchy, Rancho Palos Verdes, CA (US)

(73) Assignee: ENT INNOVATIONS INC., Redondo Beach, CA (US)

( * ) Notice: Subject to any disclaimer, the term of this patent is extended or adjusted under 35 U.S.C. 154(b) by 0 days.

(21) Appl. No.: 19/655,768

(22) Filed: Apr. 23, 2026

Related U.S. Application Data

(60) Provisional application No. 63/817,203, filed on Jun. 3, 2025.

(51) Int. Cl.
*A61F 5/08* (2006.01)

(52) U.S. Cl.
CPC .................................... *A61F 5/08* (2013.01)

(58) Field of Classification Search
CPC ...... A61F 2007/0006; A61F 5/08; A61F 5/56; A61F 2013/00476; A61M 29/00; A61M 15/08; A61M 2210/0618
See application file for complete search history.

(56) References Cited

U.S. PATENT DOCUMENTS 9,204,988 B1 12/2015 Fischell
10,556,095 B2 2/2020 Castillo
10,675,174 B2 6/2020 Castillo
D1,094,711 S 9/2025 Kissick et al.
D1,095,849 S 9/2025 Kissick et al.
2003/0000521 A1* 1/2003 Beaudry ............ A61F 13/0203 128/200.24
2015/0090398 A1* 4/2015 Ierulli .................... B32B 37/18 156/264

OTHER PUBLICATIONS

Second Wind Nasal Strips <https://dreamrecovery.io/products/second-wind-nasal-strips?variant=46201497649409>, accessed Apr. 14, 2026.
Dream Recovery Second Wind Nasal Strips—Nose Strips for Breathing, Sleep and Athletic Performance—Snore Relief and Congestion Support <https://www.amazon.com/Dream-Recovery-Second-Nasal-Strips/dp/BOFHX2KNS1?th=1>, accessed Apr. 14, 2026.

* cited by examiner

*Primary Examiner* — Majid Jamialahmadi
(74) *Attorney, Agent, or Firm* — Van Court & Aldridge LLP

(57) ABSTRACT

External nasal dilators and methods for using and manufacturing the same are provided. An external nasal dilator assembly may include a spring element (e.g., a shape-memory alloy wire) having first and second ends and a central portion. A resilient tubular cushion may encapsulate at least a portion of the spring element. First and second adhesive patches may be coupled to respective ends of the spring element and configured to adhere to lateral nasal walls of a user. At least one tactile positioning element may be coupled to at least one adhesive patch to facilitate positioning of the assembly during application. The spring element may be flat for user-customized bending or pre-formed to a curved state. A non-adhesive central zone may be provided between the adhesive patches. When applied, the assembly may exert outward mechanical force on the lateral nasal walls to enlarge the nasal valve region.

19 Claims, 8 Drawing Sheets

210/212L
250/252L
230/232L
240/242L
225L
210/212R
250/252R
225R
225/222/220
230/232R
240/242R
200

θ/θn
200

220
210/212R
250/252R
225
222
222R
230/232R
240/242R
225L
222L
210/212L
250/252L
230/232L
240/242L
200

EXTERNAL NASAL DILATORS

CROSS-REFERENCE TO RELATED APPLICATION(S)

This application claims the benefit of prior filed U.S. Provisional Patent Application No. 63/817,203, filed Jun. 3, 2025, which is hereby incorporated by reference herein in its entirety.

COPYRIGHT NOTICE

At least a portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyright rights whatsoever.

TECHNICAL FIELD

This disclosure relates to external nasal dilators and methods of using and manufacturing the same.

BACKGROUND OF THE DISCLOSURE

Nasal obstruction is a common condition that can significantly impair sleep quality, physical performance, daytime cognition, and respiratory efficiency. Numerous studies have shown that improving nasal air flow can reduce nasal congestion, snoring, and sleep-disordered breathing as well as improve cognitive and physical performance. Therefore, systems and methods for improving the opening of nasal passageways are desired.

SUMMARY OF THE DISCLOSURE

This document describes external nasal dilators and methods of using and manufacturing the same.

For example, an external nasal dilator assembly is provided that includes a spring subassembly, which includes a spring body including a spring body central portion extending between a first spring body end and a second spring body end, and a cushion component about the spring body along at least a portion of the spring body central portion, a first adhesive patch coupled to a first spring subassembly end of the spring subassembly, and a second adhesive patch coupled to a second spring subassembly end of the spring subassembly.

This Summary is provided to summarize some example embodiments, so as to provide a basic understanding of some aspects of the subject matter described in this document. Accordingly, it will be appreciated that the features described in this Summary are only examples and should not be construed to narrow the scope or spirit of the subject matter described herein in any way. Unless otherwise stated, features described in the context of one example may be combined or used with features described in the context of one or more other examples. Other features, aspects, and advantages of the subject matter described herein will become apparent from the following Detailed Description, Figures, and Claims.

BRIEF DESCRIPTION OF THE DRAWINGS

The discussion below makes reference to the following drawings, in which like reference characters may refer to like parts throughout, and in which.

DETAILED DESCRIPTION OF THE DISCLOSURE

Figure 1:
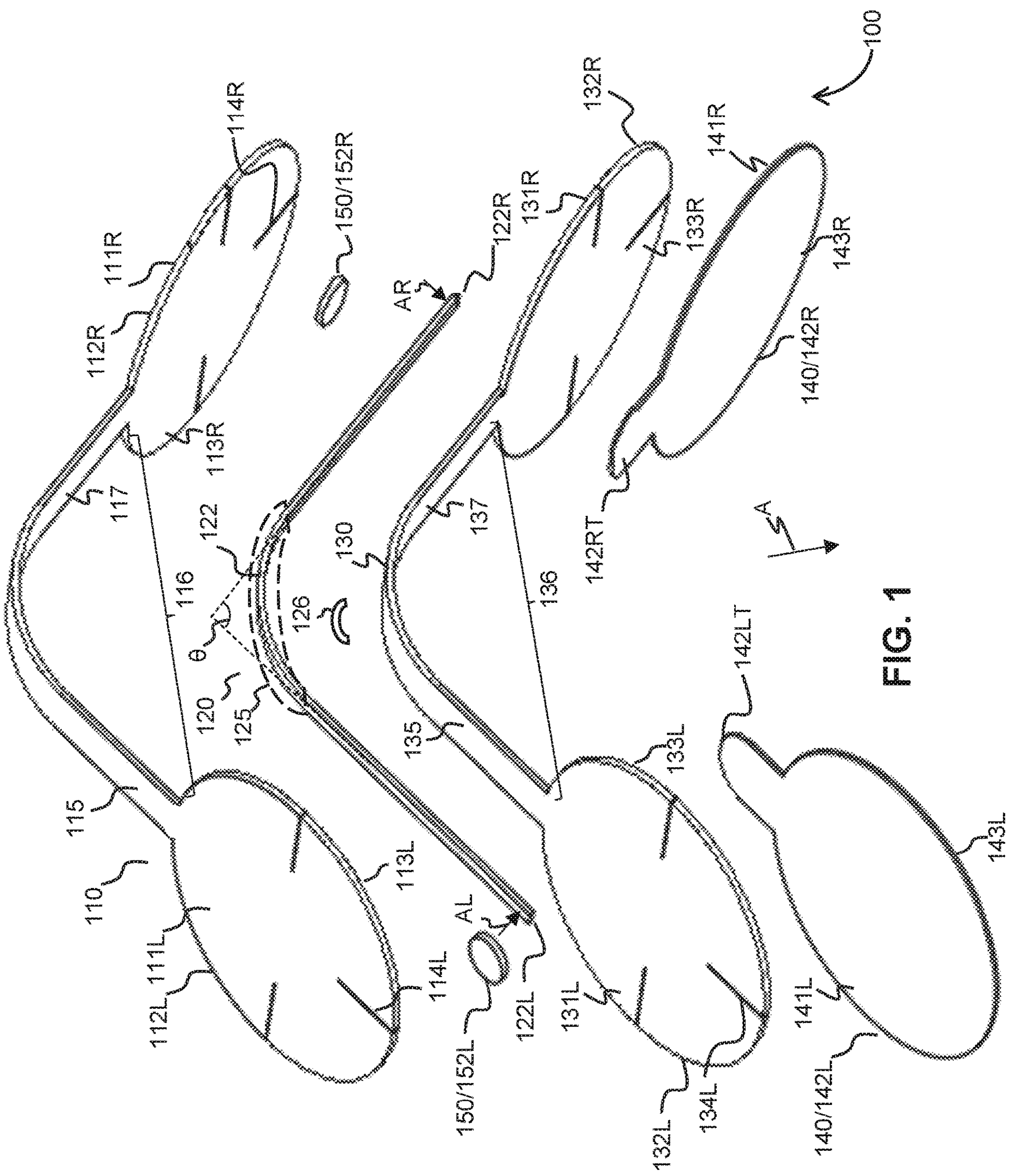
FIG. 1 illustrates an exploded perspective view of a nasal dilation assembly in a natural state, according to one or more embodiments of the disclosure.
Figures 1A, 1B, 1C:
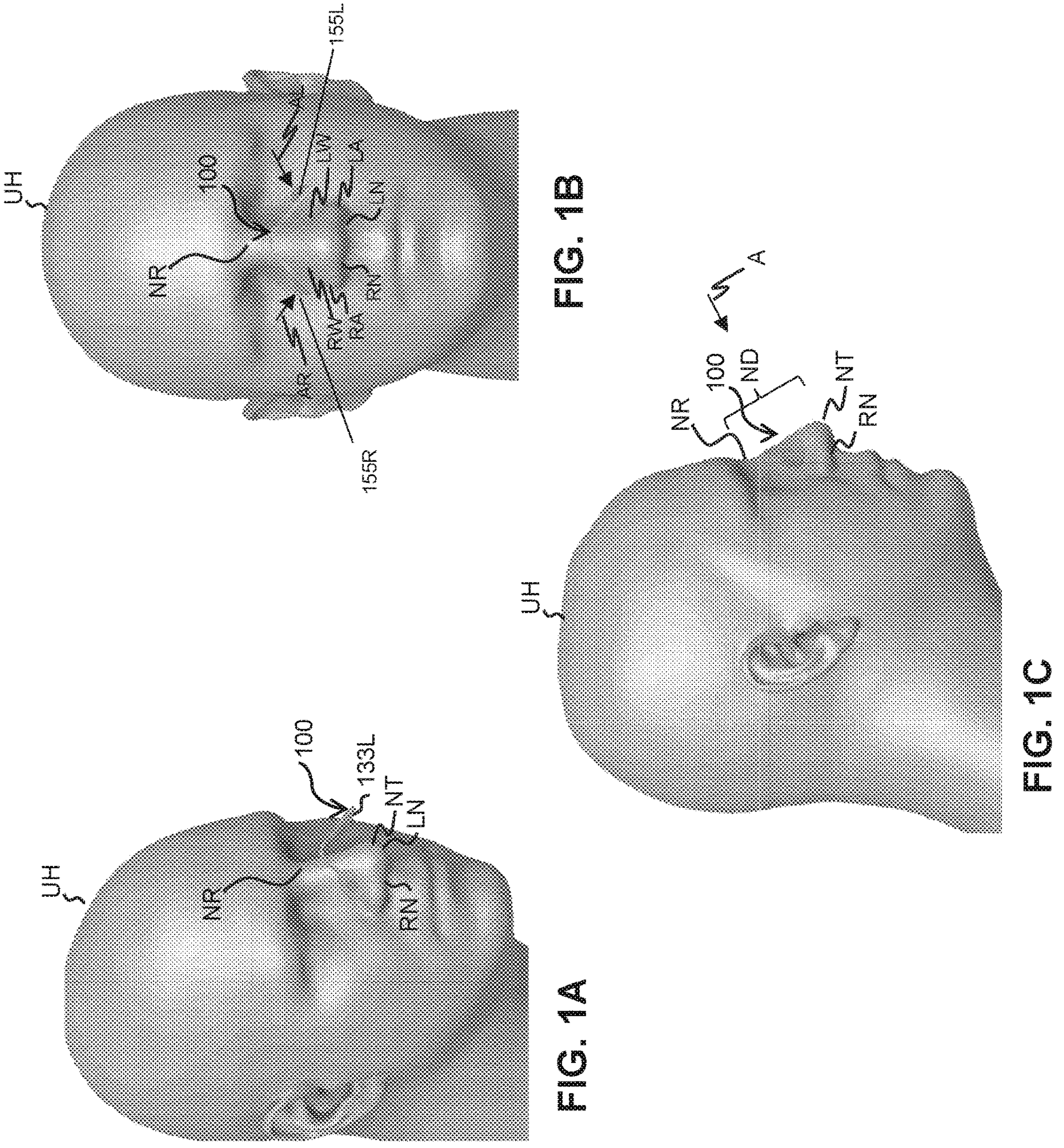
FIG. 1A illustrates another perspective view of the nasal dilation assembly of FIG. 1 in its natural state adjacent a user's head, according to one or more embodiments of the disclosure.
FIG. 1B illustrates a front view of the nasal dilation assembly of FIGS. 1 and 1A in its natural state adjacent the user's head of FIG. 1A, according to one or more embodiments of the disclosure.
FIG. 1C illustrates a side view of the nasal dilation assembly of FIGS. 1, 1A, and 1B in its pinched state on the user's head of FIGS. 1A and 1B, according to one or more embodiments of the disclosure.

The present disclosure relates generally to external nasal dilators and methods for using and manufacturing the same.

To address nasal airflow restriction, external nasal dilators may be used because of their non-invasive nature and low cost. Some external nasal dilators may use an adhesive backing along a portion or the entirety of an interior side of a spring element (e.g., a flexible plastic or metal spring structure or strip, which may be straight or curved in its native state) that may secure the spring element across the bridge of the nose of a user. When the spring element is bent around the structure of a user's nose for securing the ends of the spring element to opposite sides of the user's nose (e.g., just above the left nasal ala and right nasal ala), the spring element may attempt to return to its native shape and exert a relatively constant outward spring force to the lateral nasal walls. While airway patency may be improved, such a design may have certain limitations, as the central portion of such a spring element will become the fulcrum for the lateral opening forces and will create a compressive force that will uncomfortably push into the skin of the user's nasal dorsum. The mechanical recoil forces generated may be limited by how much the spring element is bent from its native state around a user's nasal dorsum. Such force may be fixed given that the central fulcrum portion has an underlying adhesive that will stick to the nasal dorsum skin. In some embodiments, an external nasal dilator assembly may include a memory-shaped spring structure that may be provided with an adhesive patch coupled at each end of the spring structure for securing the assembly to opposite sides of the user's nose. The assembly may include a central bridge portion extending between the adhesive patches, where the bridge portion is without adhesive, and does not stick to the user's nose. A tactile element may be provided on an exterior side of one or each patch to enable easier one handed handling and placement of the assembly. The spring structure may be a metal alloy spring structure, which may be configured to provide a curved native state. The curved shape and/or the metal alloy composition of the spring structure may provide increased mechanical leverage or mechanical advantage and/or improved directionality of nasal passageway opening forces compared to other designs (e.g., an assembly with a naturally flat plastic band rather than a naturally curved metal spring). In some embodiments, an external nasal dilator assembly may include a spring element extending between a first end and a second end (e.g., any suitable structure that may be plastic or metal or the like and that may be straight or curved between its ends in its native state (e.g., a shape-memory alloy wire)), a cushion extending about at least a portion of the spring element between the first end of the spring element and the second end of the spring element (e.g., a resilient tubular cushion with a non-adhesive exterior surface that encapsulates a portion or the entirety of the spring element), a first adhesive patch coupled to the first end of the spring element and configured to adhere to a first lateral nasal wall of a user, and a second adhesive patch coupled to the second end of the spring element and configured to adhere to a second lateral nasal wall of the user. A tactile positioning element may be coupled to the first adhesive patch and configured to provide a tactile indication detectable by the user to facilitate positioning of the assembly during application of the assembly on the lateral nasal walls of the user.

As shown in FIGS. 1, 1A, 1B, and 1C, a nasal dilation assembly 100 may include an exterior subassembly 110, a spring subassembly 120, and an interior subassembly 130. Spring subassembly 120 may include a spring body 122 that may extend between a left spring end 122L and a right spring end 122R. As shown in FIG. 1, spring body 122 may be pre-configured to have a natural state that forms any suitable curvature that may be defined by any suitable angle θ that may be any suitable value or in any suitable range of values, such as 50° to 230° or 50° to 90° or the like. Alternatively, the spring element will arrive flat with users able to bend the central portion of the spring body to create a customized fit for the shape of their own nose. Body 122 may be configured to spring back towards or otherwise attempt to return to its natural state from any suitable pinched state, where such a pinched state may be achieved when ends 122L and 122R are pinched towards each other through application of user pressure in the directions of application arrows AL and AR, respectively. For example, a user's right thumb may press with any suitable user force on end 122R in the direction of arrow AR and the user's right index finger may press with any suitable force on end 122L in the direction of arrow AL when attempting to secure assembly 100 to the user's nose in order to achieve a pinched state, and body 122 may be configured to exert opposing forces with end 122L in a direction opposite to arrow AL and with end 122R in a direction opposite to arrow AR to attempt to return body 122 from any suitable pinched state to its natural state. Spring body 122 may be made of any suitable material or combination of materials, including, but not limited to, rubber, plastic, alloy, metal, metal alloy, Nitinol alloys, beta Titanium alloys, Copper, Zinc, Copper-Zinc alloys or Brass, Aluminum, Nickel, Copper-Zinc-Aluminum alloys, Copper-Aluminum-Nickel alloys, Iron-based shape-memory alloys, Cobalt-Nickel-Aluminum alloys, any other binary, ternary, or quaternary shape-memory alloy compositions, spring steel, stainless steel, Beryllium Copper, Phosphor Bronze, any other suitable shape memory alloy ("SMA"), and/or the like, with any suitable density (e.g., a density in the range of 4.0-8.0 grams per cubic centimeter). Body 122 may have any suitable cross-sectional geometry, such as, for example, a cross-sectional thickness of about 0.4 millimeters and a cross-sectional width of about 0.8 millimeters, while a length of body 122, and/or any other dimension(s) thereof, may be chosen based on the size of the user to wear assembly 100 (e.g., an SMA wire of any suitable length and/or cross-section). Any suitable characteristics of body 122 (e.g., cross-sectional width, cross-sectional thickness, bend radius, etc.) may be customized to exert any desired force(s). In some embodiments, spring body 122 may be a pre-formed structure or a flat structure (e.g., later to be bent and customized by a user), a memory-shaped metal alloy structure, or the like. In some embodiments, spring subassembly 120 may include any suitable cushion component 125, such as any suitable coating or overmold that may be provided about any suitable portion or the entirety of spring body 122. For example, as shown, cushion component 125 may be provided about spring body 122 along a central portion of spring body 122 (e.g., a tubular (e.g., straight or curved) cushion that may encapsulate the longitudinal periphery of a central portion of spring body 122 between its ends 122L and 122R but not including the ends of spring body 122 and/or but not including the end portions of spring body 122 that may be held between respective patches 112 and 132). Alternatively, cushion component 125 may be provided about the entirety of spring body 122 (e.g., for adhering to and encapsulating the entire structure of spring body 122). Cushion component 125 may be provided by any suitable material or combination of materials, including, but not limited to, silicone, foam, silicone foam, plastic, rubber, a biocompatible soft polymer overmold, silicone rubber, thermoplastic polyurethane/polyethylene, and/or the like. Cushion component 125 may be configured to provide any suitable cushion or comfort to a user's head UH (e.g., to the nasal dorsum ND extending along the front of a user's nose between its nasal root NR and its nasal tip NT) if the center of assembly 100 were to contact and push up against the front of the user's nose.

Interior subassembly 130 may include a left interior patch 132L and a right interior patch 132R. In some embodiments, interior subassembly 130 may also include a central interior bridge 136 that may extend between patch 132L and patch 132R. Subassembly 130 (e.g., patch 132L, patch 132R, and/or bridge 136) may be made of any suitable material or combination of materials, including, but not limited to, paper, coated paper, plastic or plastic films (e.g., polyvinyl chloride ("PVC"), polyethylene ("PE"), polypropylene ("PP"), polyurethane ("PU"), polyethylene terephthalate ("PET"), etc.), nonwoven fabrics, woven fabrics, foam materials, latex, silicone, and/or the like. Left interior patch 132L may provide a left interior patch exterior surface 131L and an opposing left interior patch interior surface 133L, while right interior patch 132R may provide a right interior patch exterior surface 131R and an opposing right interior patch interior surface 133R. Each interior patch may be any suitable shape and any suitable size such that its interior patch exterior surface may contact a respective end region of spring body 122 and such that its interior patch interior surface may contact a portion of a respective lateral nasal wall of a user's nose (e.g., left interior patch 132L may be configured to provide left interior patch exterior surface 131L for contacting a left end region of body 122 (e.g., a region adjacent to if not also including end 122L) and left exterior patch exterior surface 133L for contacting a left lateral nasal wall LW of a user's nose, while right interior patch 132R may be configured to provide right interior patch exterior surface 131R for contacting a right end region of body 122 (e.g., a region adjacent to if not also including end 122R) and right exterior patch exterior surface 133R for contacting a right lateral nasal wall RW of a user's nose). At least a portion of each one of left interior patch interior surface 133L and right interior patch interior surface 133R may be provided by or with any suitable adhesive that may be configured to stick to the skin of a user (e.g., the skin of a user's lateral nasal wall (e.g., just above a nasal ala (e.g., lateral nasal wall RW just above nasal ala RA of nostril RN or lateral nasal wall LW just above nasal ala LA of nostril LN))) when assembly 100 is pinched onto a user's nose. Such an adhesive may be made of any suitable material or combination of materials, including, but not limited to, any suitable pressure-sensitive glue, acrylic-based pressure-sensitive adhesives (e.g., methacrylate copolymers), rubber-based pressure-sensitive adhesives (e.g., natural rubber, synthetic rubber, styrene-isoprene-styrene ("SIS") block copolymers, rubber-based polymers, etc.), silicone-based pressure-sensitive adhesives, hydrocolloid adhesives, and/or the like, which may be mixed with fillers, resins, and/or silicone that may be designed to stick to skin but allow gentle removal therefrom. At least a portion of each one of left interior patch exterior surface 131L and right interior patch exterior surface 131R may be provided by or with any suitable adhesive that may be configured to stick to a portion of spring subassembly 120 and/or an opposing patch (e.g., a patch of any suitable exterior subassembly 110) when assembly 100 is fully assembled. Such an adhesive may be made of any suitable material or combination of materials, including, but not limited to, any suitable material(s) that may be used for the interior patch interior surfaces or otherwise. One or each of left interior patch 132L and right interior patch 132R may include one or more slits formed therethrough (e.g., one or more slit(s) 134L formed through patch 132L and its surfaces 131L and 133L and/or one or more slit(s) 134R formed through patch 132R and its surfaces 131R and 133R), where each slit may enable the patch to more closely conform to the shape of the portion of the user's nose against which the patch may be pressed for adherence. One or more slits may be configured in any suitable manner or pattern, such as radially and/or angularly from a center of the patch to enable any suitable conformity with any suitable geometry of a user's face. When included, central interior bridge 136 may include an interior bridge exterior surface 135 and an interior bridge interior surface 137. At least a portion of an interior bridge exterior surface 135 (e.g., like each one of left interior patch exterior surface 131L and right interior patch exterior surface 131R) may be provided by or with any suitable adhesive that may be configured to stick to a portion of spring subassembly 120 and/or an opposing bridge of another subassembly (e.g., a bridge of any suitable exterior subassembly 110) when assembly 100 is fully assembled. Such an adhesive may be made of any suitable material or combination of materials, including, but not limited to, any suitable material(s) that may be used for the interior patch interior surfaces or otherwise. It is to be understood that, in most embodiments, interior bridge interior surface 137 (e.g., unlike each one of left interior patch interior surface 133L and right interior patch interior surface 133R) may be provided by or with any suitable non-adhesive material that may not stick to a user's skin if any contact with such skin is made (e.g., the front of a nasal dorsum), but instead the material of interior bridge interior surface 137 may be configured to provide any suitable non-adhering and comfortable surface for any possible interface with a user's skin. Such a non-adhering interior bridge interior surface 137 may provide an interior portion of interior subassembly 130 that does not have adhesive (e.g., unlike surfaces 143L and 143R), which may provide a non-sticky handling zone of the interior surface of assembly 100 (e.g., after any liner subassembly 140 has been removed) that may enable simplified placement, alignment, and application of assembly 100 onto a user's face without that non-sticky handling zone (e.g., the central bridge region of assembly 100) sticking to the user's face. Moreover, such mechanical decoupling due to such a non-adhering interior bridge interior surface 137 may reduce or prevent damping of spring force, thereby enabling more efficient force transmission during assembly use, and/or thereby reducing shear stress during assembly removal.

Assembly 100 may also include a liner subassembly 140 that may include a left liner patch 142L and a right liner patch 142R. Subassembly 140 (e.g., patch 142L and 142R) may be made of any suitable material or combination of materials, including, but not limited to, adhesive liner, paper, coated paper, plastic or plastic films (e.g., PVC, PE, PP, PU, PET, etc.), nonwoven fabrics, woven fabrics, foam materials, latex, silicone, and/or the like. Left liner patch 142L may provide a left liner patch exterior surface 141L and an opposing left liner patch interior surface 143L, while right liner patch 132R may provide a right liner patch exterior surface 141R and an opposing right liner patch interior surface 143R. Each liner patch may be any suitable shape and any suitable size such that its liner patch exterior surface 141 may contact and cover at least a portion if not all of an opposing exterior patch exterior surface to protect the adhesive portion of that exterior patch exterior surface 133 until it is ready for use. Each liner patch may include a liner tab (e.g., tab 142LT of patch 142L and tab 142RT of patch 142R) that may be configured to enable easy peeling by the user of the liner patch from the remainder of assembly 100 when the adhesive of exterior patch exterior surfaces 133L and 133R are to be exposed and used for adhering assembly 100 to a user's face. Therefore, the material of at least left liner patch exterior surface 141L and right liner patch exterior surface 141R may be configured to easily peel away from respective exterior patch exterior surfaces 133L and 133R without compromising the effectiveness of the adhesive qualities of exterior patch exterior surfaces 133L and 133R. The material of left liner patch interior surface 143L and right liner patch interior surface 143R may be any suitable material that may be non-adhesive in order for assembly 100 to be stored prior to use without its exposed interior surface(s) sticking to undesired objects.

In some embodiments, spring subassembly 120 may be coupled to interior subassembly 130 using any suitable adhesive that may be provided by any suitable exterior surface(s) of interior subassembly 130 (e.g., any suitable adhesive of left interior patch exterior surface 131L, any suitable adhesive of right interior patch exterior surface 131R, and/or any suitable adhesive of any interior bridge exterior surface 135). Additionally or alternatively, spring subassembly 120 may be coupled to interior subassembly 130 using any suitable exterior subassembly 110, which may be coupled to interior subassembly 130 for sandwiching at least a portion of spring subassembly 120 therebetween. For example, exterior subassembly 110 may include a left exterior patch 112L and a right exterior patch 112R. In some embodiments, exterior subassembly 110 may also include a central exterior bridge 116 that may extend between patch 112L and patch 112R. Subassembly 110 (e.g., patch 112L, patch 112R, and/or bridge 116) may be made of any suitable material or combination of materials, including, but not limited to, adhesive liner, paper, coated paper, plastic or plastic films (e.g., PVC, PE, PP, PU, PET, etc.), nonwoven fabrics, woven fabrics, foam materials, latex, silicone, and/or the like. Left exterior patch 112L may provide a left exterior patch exterior surface 111L and an opposing left exterior patch interior surface 113L, while right exterior patch 112R may provide a right exterior patch exterior surface 111R and an opposing right exterior patch interior surface 113R, and/or while central exterior bridge 116 may provide a central exterior bridge exterior surface 115 and an opposing central exterior bridge interior surface 117. The material of left exterior patch exterior surface 111L, right exterior patch exterior surface 111R, and/or any central exterior bridge exterior surface 115 may be any suitable material that may be non-adhesive in order for assembly 100 to be stored prior to use without its exposed exterior surface(s) sticking to undesired objects. The material of left exterior patch interior surface 113L, right exterior patch interior surface 113R, and/or any central exterior bridge interior surface 117 may be any suitable material that may be adhesive in order for the interior of exterior subassembly 110 to be coupled to the exterior of interior subassembly 130, which may or may not include its own adhesive material. Alternatively, the material of left exterior patch interior surface 113L, right exterior patch interior surface 113R, and/or any central exterior bridge interior surface 117 may be any suitable material that may be non-adhesive but that may still enable the interior of exterior subassembly 110 to be coupled to the exterior of interior subassembly 130 if the exterior of interior subassembly 130 includes its own adhesive material and/or if an independent adhesive material is provided between subassembly 110 and subassembly 130 for coupling the two subassemblies together (e.g., an outer surface of spring body 122 and/or cushion component 125 may be provided with adhesive for interfacing with and coupling to subassembly 110 and/or subassembly 130). Each exterior patch may be any suitable shape and any suitable size such that its exterior patch interior surface may contact a respective end region of spring body 122 and/or a respective portion of an opposing interior patch exterior surface. For example, left exterior patch 112L may be configured to provide left exterior patch interior surface 113L for contacting a left end region of body 122 (e.g., a region adjacent to if not also including end 122L) and/or an opposing interior patch exterior surface 131L of patch 132L, such that a left end region of body 122 may be sandwiched between patch 112L and patch 132L, whereby an adhesive of surface 113L and/or an adhesive of surface 131L may couple patch 112L to patch 132L and retain a left end region of body 122 (e.g., end 122L) therebetween. Additionally, right exterior patch 112R may be configured to provide right exterior patch interior surface 113R for contacting a right end region of body 122 (e.g., a region adjacent to if not also including end 122R) and/or an opposing interior patch exterior surface 131R of patch 132R, such that a right end region of body 122 may be sandwiched between patch 112R and patch 132R, whereby an adhesive of surface 113R and/or an adhesive of surface 131R may couple patch 112R to patch 132R and retain a right end region of body 122 (e.g., end 122R) therebetween. Additionally, in some embodiments, central exterior bridge 116 may be configured to provide central exterior bridge interior surface 117 for contacting a central region of spring body 122 and/or an opposing interior bridge exterior surface 135 of interior bridge 136, such that a central region of body 122 may be sandwiched between exterior bridge 116 and interior bridge 136, whereby an adhesive of surface 117 and/or an adhesive of surface 135 may couple bridge 116 to bridge 136 and retain a central region of body 122 therebetween. Therefore, any suitable adhesive provided along any suitable interior portion(s) of exterior subassembly 110 and/or any suitable adhesive provided along any suitable exterior portion(s) of interior subassembly 130 may be used to couple interior subassembly 130 to exterior subassembly 110 while retaining at least a portion of spring subassembly 120 therebetween. In some embodiments, in addition to or as an alternative to cushion component 125 that may be provided about a central region of spring body 122, any suitable cushion element(s) 126 may be positioned between bridge 136 and spring body 122 and held therebetween through any coupling between interior subassembly 130 and body 122 and/or through any coupling between interior subassembly 130 and exterior subassembly 110, such that cushion element(s) 126 may provide any suitable cushion interface between spring body 122 and a user's face when wearing assembly 100 (e.g., a cushion interface that may not be provided by bridge 136 without cushion 126). One or each of left exterior patch 112L and right exterior patch 112R may include one or more slits formed therethrough (e.g., one or more slit(s) 114L formed through patch 112L and its surfaces 111L and 113L and/or one or more slit(s) 114R formed through patch 112R and its surfaces 111R and 113R), where each exterior subassembly slit (e.g., slit(s) 114L/114R) may align with each interior subassembly slit (e.g., slit(s) 134L/134R) such that the aligned slits may enable the aligned interior/exterior patches to more closely conform to the shape of the portion of the user's nose against which the interior patch may be pressed for adherence. One or more slits may be configured in any suitable manner or pattern, such as radially and/or angularly from a center of the patch to enable any suitable conformity with any suitable geometry of a user's face.

Assembly 100 may include any suitable tactile subassembly 150 that may be provided to enable a user to locate and manipulate appropriate portions of assembly 100 for deforming spring subassembly 120 from its natural state to a pinched state for coupling to a user's face. For example, subassembly 150 may include a left tactile element 152L and/or a right tactile element 152R. In some embodiments, left tactile element 152L may be sandwiched between exterior patch 112L and spring body end 122L, and/or right tactile element 152R may be sandwiched between exterior patch 112R and spring body end 122R, such that when assembly 100 is fully assembled, a user may be able to feel a tactile element through an exterior patch, which may enable the user to locate an appropriate portion of spring body 122 for reconfiguring spring body 122 from its natural state to a pinched state. For example, in some embodiments, each one of tactile elements 152L and 152R may be provided as a soft silicon bead (e.g., half-sphere bead) or any other suitable soft material (e.g., a material that may be provided as a liquid during assembly of assembly 100 and that may then set to a solid at room temperature), where each tactile element may be configured to cover an end of spring body 122 (e.g., a sharp edge of a spring wire) and create a protrusion (e.g., a bump) at a portion of a patch of exterior subassembly 110 for enabling easy user handling. In some embodiments, where assembly 100 may not include an exterior subassembly 110, a tactile element may be contacted directly by a user during handling and coupling of assembly 100 to a user's face (e.g., a tactile component may be coupled to a patch 132 and contacted by a user. In some embodiments, a tactile element may be configured to at least partially couple an end region of spring body 122 to a patch of interior subassembly 130 and/or to a patch of exterior subassembly 110. When assembly 100 has been fully assembled and ready for use, a user may use right tactile element 152R to enable their right thumb to locate end 122R and press with any suitable user force on element 152R and end 122R in the direction of arrow AR (e.g., at a bump 155R caused by element 152R), and user may use left tactile element 152L to enable their right index finger to locate end 122L and press with any suitable force on element 152L and end 122L in the direction of arrow AL (e.g., at a bump 155L caused by element 152L) when attempting to secure assembly 100 to the user's nose in order to achieve a pinched state.

As shown, once assembled and ready for use (e.g., once any liner subassembly 140 has been removed), assembly 100 may be moved in the direction of arrow A towards the user's face such that the interior surfaces of interior subassembly 130 may be positioned just adjacent to but not contacting the user's face (see, e.g., the position of FIGS. 1A and 1B) and then assembly 100 (e.g., spring subassembly 120) may be reconfigured from its natural state to a pinched state, such as by a user simultaneously applying a pinch force in the direction of arrow AR on or near feature 152R/end 122R and a pinch force in the direction of arrow AL on or near feature 152L/end 122L, whereby at least a portion of interior patch interior surface 133L of left interior patch 132L of interior subassembly 130 may contact and stick to left lateral nasal wall LW of the user's nose and at least a portion of interior patch interior surface 133R of right interior patch 132R of interior subassembly 130 may contact and stick to right lateral nasal wall LR of the user's nose, and whereby a portion of interior bridge interior surface 137 may or may not contact a portion of nasal dorsum ND of the user's nose, where any such contact may not include adhering surface 137 to the user's nose. Then, once the user terminates such a pinch force on assembly 100, spring assembly 120 may attempt to reconfigure itself from the pinched state back to its natural state. However, due to the adhesion of assembly 100 to the user's face (e.g., adhesion of interior patch interior surface 133L of left interior patch 132L of interior subassembly 130 to left lateral nasal wall LW of the user's nose and adhesion of interior patch interior surface 133R of right interior patch 132R of interior subassembly 130 to right lateral nasal wall LR of the user's nose), such a reconfiguration attempt may be limited. For example, while the pinching may reduce natural state angle θ of spring subassembly 120 from 100% of natural state angle θ in the natural state of assembly 100 of FIGS. 1, 1A, and 1B (or the preformed natural state as customized by the user (e.g., if the spring subassembly may be delivered to an end user flat or any other suitable delivered natural state and then reconfigured to a user customized natural state by a user before use)) (e.g., natural state angle θn (e.g., as delivered or as preformed as customized by the user after delivery)) to any suitable pinched reduced percentage of angle θ (e.g., 30%-90% or 60% or any other suitable percentage of angle θn (i.e., a pinched reduced angle θp)) in the pinched state of assembly 100 of FIG. 1C, the termination of a pinching force but addition of an adhesion force on assembly 100 may enable an increase of the angle of spring subassembly 120 from its pinched reduced percentage of angle θn in its pinched state to any suitable adhered reduced percentage of angle θ (e.g., 70%-80% or 75% or any other suitable percentage of angle θn (i.e., an adhered interim angle i)) in its adhered state (e.g., where an adhered interim angle θi may be greater than pinched reduced angle θp but less than natural state angle θn). This reconfiguration of assembly 100 from the pinched state and pinched reduced angle θp to the adhered state and adhered interim angle θi that may be any suitable angle greater than pinched reduced angle θp while interior patches 132L and 132R remain adhered to lateral nasal walls LW and RW may enable assembly 100 to exert outward mechanical forces on the user's nose (e.g., expansion forces that may be in directions opposite to the directions of arrows AL and AR) to enlarge the nasal valve region of the user's nose (e.g., the geometry and configuration of spring body 122 along with the adhesion properties of interior subassembly 130 may provide two enhanced torque vectors, each of which may be normal to a respective an airway lumen and may increase an airway opening).

Therefore, assembly 100 may provide an improved nasal strip design that increases the mechanical efficiency of airway dilation while reducing the dermatologic and handling limitations of various prior designs. Improvements may include increased mechanical leverage without increased user discomfort, improved directionality of opening force, simplified handling during application, and a meaningful reduction in the total adhesive contact area with the skin. A device capable of achieving these improvements while remaining non-invasive and externally applied represents a significant advancement in nasal dilation technology. Assembly 100 may incorporate features that make the assembly easier to handle and position on the nose for simplifying its application, such as with a non-adhering interior bridge interior surface 137 and/or with tactile subassembly 150 and/or with slits 114/134. Assembly 100 may minimize the amount of skin exposed to adhesive to help prevent irritation and make the assembly suitable for a wider range of users, such as with a non-adhering interior bridge interior surface 137. Assembly may increase the force or leverage applied to gently open the nasal airway to improve airflow (e.g., increased mechanical leverage without increased user discomfort), which may be enabled by a spring body made of a robust material (e.g., a metal alloy) and configured with a curved natural state.

Therefore, this disclosure provides an externally placed nasal dilation device or external nasal dilator or external nasal dilator assembly that may be provided with an internal memory spring structure. The external nasal dilator may include a non-adhesive central segment positioned between two opposing adhesive end segments (e.g., surface 137 between surfaces 133L and 133R). The external nasal dilator may be configured to open mechanically the nasal valve region with a higher torque efficiency while reducing dermatologic injury compared to other possible solutions.

An external nasal dilator is disclosed that may include a flexible shape memory alloy spring element configured to exert an outward mechanical force to enlarge the nasal valve region. The device may include a non-adhesive central segment positioned between two opposing adhesive end segments. The non-adhesive region (e.g., surface 137) may provide a handling zone for simplified placement and alignment. This reduces the total adhesive-skin contact area and minimizes skin irritation and trauma associated with adhesive removal. The memory metal spring element geometry provides an enhanced torque vector that is normal to the airway lumen and increases airway opening relative to a plastic adhesive-only nasal strip. The adhesive end segments may optionally include angular or radial slits that may permit the adhesive to bend locally and perfectly conform to a user's unique nasal anatomy. Fit, seal, and mechanical efficiency are optimized with the design. The device increases airflow in users with high resistance nasal valve collapse while reducing skin injury associated with consistent use.

This disclosure provides an improved external nasal dilator strip configured to increase the magnitude and efficiency of nasal valve opening force while simultaneously reducing dermatologic complications associated with large-area adhesives. In some embodiments, the assembly may include a central non-adhesive region positioned between two spaced apart adhesive end regions (e.g., surface 137 between surfaces 133L and 133R), wherein a resilient memory metal spring element may extend across at least a portion of the length of the strip. The central non-adhesive region creates an adhesion void directly over the nasal bridge, thereby enabling increased deflection amplitude and torque transfer to the lateral nasal wall structures during use. This arrangement redirects force vectors more normal to the nasal airway lumen, resulting in enhanced nasal dilation compared to continuous adhesive strips.

The non-adhesive region may provide a non-tacky handling surface that may simplify placement and alignment and markedly reduce skin exposure to adhesives. The adhesive end sections may include engineered slit geometries configured to locally articulate and conform to individual patient nasal curvature, thereby improving retention, comfort, and personalization of fit. By limiting adhesive contact to the end regions only, the assembly may reduce pain and trauma during removal, lower skin irritation risk during repeated nightly use, and/or improve user compliance. Therefore, assembly 100 may provide improved mechanical performance, improved usability, improved comfort, and improved safety without increasing device complexity or invasiveness. A plurality of embodiments, materials, geometries, and spring configurations are possible within the scope of the disclosure as described herein.

The present disclosure introduces an innovative approach to enhance nasal strips by incorporating a non-adhesive segment positioned centrally between two adhesive end sections (e.g., surface 137 between surfaces 133L and 133R). In some embodiments, a thin silicone, soft plastic, silicone foam, rubber film, or similar material (e.g., cushion component 125 (e.g., with a non-adhering exterior surface)) may be applied over a memory-shaped metal spring body 122 in the central region of the assembly, which may provide added comfort if the central region were to rub up against the nasal dorsum of the user. This modification offers several notable benefits: memory-shaped metal body and central adhesion void may increase the mechanical force or torque exerted by the assembly to help open nasal airway more effectively, provide better force directions normal to the nasal airway, reduce discomfort during removal, simplify application by providing a non-sticky area for handling, and/or minimize the amount of skin exposed to adhesive, thereby reducing the risk of irritation, especially during prolonged use such as overnight wear.

Accordingly, an objective of an assembly of this disclosure is to enhance the force and direction applied by the nasal strip, thereby improving the dilation of the nasal passages and facilitating easier breathing. Another goal is to enhance user comfort by making the removal process gentler and less likely to cause skin irritation. Additionally, the presence of a non-adhesive central area may allow for easier handling and more precise placement of the strip on the nose. Finally, by limiting adhesive contact to only the ends of the strip, the overall area of skin subjected to potential irritation may be significantly reduced. Slits on the adhesive patches may allow for the adhesive portion of the strip to contour around the individual curves of a user's nose providing a customized fit.

The assembly may employ a high performance material that may generate torque while providing adhesion to the skin where necessary. The adhesive patches may be designed to allow consistent optimal placement of the assembly with a single hand. For example, through the use of silicone beads or any other suitable tactile subassembly 140 that may be stuck external to an exterior non-adhesive layer (e.g., exterior surfaces 111L and 111R) or that may be sandwiched between exterior subassembly 110 and interior subassembly 130, one or more bumps may be provided that a user can grasp between their fingers (e.g., silicone or other substances to create a protrusion that allows a user to grab on to the assembly easily with one hand).

Assembly 100, which may be referred to herein as a "NoseVent", may include an externally placed shape memory metal alloy spring that may sit over the mid-nasal dorsum. A curved shaped metal alloy may be anchored to the lateral nasal wall with an adhesive. When users are ready to use the product, paper (e.g., liner subassembly 140) underlying the adhesive may be removed and limbs of the spring may be compressed by pinching small silicone tabs (e.g., tactile subassembly 140) on the outside of an adhesive tape. Upon loading the spring, the adhesive tape (e.g., surfaces 133L/133R) may be placed upon the lateral nasal walls (e.g., immediately below the nasal bones). Following placement, the spring may unload providing lateral opening for both the internal and external nasal valves. Unlike other products, no pressure may develop at the skin overlying the nasal dorsum, thereby enabling more comfortable use of the product. This may dilate the nose and improve nasal airflow. The assembly may act specifically to dilate the internal and external nasal valves. The internal nasal valve may be the connection point between the nasal septum and the upper lateral cartilage. The external nasal valve may be the side portion of the nostril.

Spring body 122 may be bent and programmed to provide tunable force (torque) and direction. Due to any suitable metal alloy density that may be used to provide spring body 122, it may be lighter than other solutions, thereby enhancing user comfort and experience. The metal alloy may be covered with silicone, soft plastic, or rubber (e.g., any portion(s) or all of body 122 may be covered by component 125 (or through use of element 126)) that may function in any suitable ways, including, but not limited to, providing comfort between the center portion of the device and the nose bridge, creating separation between the device and the nose bridge, enhancing the force exerted at the ends of the assembly (e.g., higher fulcrum), creating a non-adhesive interface between assembly 100 and nasal dorsum ND, creating a separation between the adhesive patches and the plastic covered metal alloy (e.g., creates a pocket (e.g., deadspace between metal and skin)), and/or the like. If component 125 and/or element 126 extends along body 122 to one or both of ends 122L and 122R or at least to a portion of body 122 at one or both of patches 132L and 132R, then such component 125/126 may create a pocket air-gap separation zone between that portion of body 122 and patch 132L/132R if not also between that portion of body 122 and patch 112L/112R (e.g., a void where adhesive may be absent), thereby increasing force amplification at the tip. Spring body 122 may include a shaped memory metal alloy wire. Spring body 122 may be pre-programmed into a defined curvature, or multiple curvature states (e.g., the angle a user may bend the spring body between their fingers (e.g., for pre-bent alternative, different products with different pre-set angles/force levels)), that when unconstrained produces a controlled outward expansion force (e.g., selectable by model, geometry, heat set programming, etc.). When the adhesive end regions are fixed to the lateral nasal skin surfaces (e.g., surfaces 143L/143R adhered to surfaces LW/RW), the spring may attempt to return to its programmed curvature (e.g., return from its pinched state to its natural state), generating torque normal to the nasal airway lumen. This may be a substantially different mechanical effect than that of a naturally flat plastic component that may only generate low amplitude bending (e.g., due to being made of metal and not being adhered in the middle to a user's head UH (e.g., to the nasal dorsum ND), as the force vectors may be more laterally oriented, whereas a flat plastic strip may have force vectors that are more vertically oriented). Spring body 122 may be made of a metal alloy that may be selected for its high strength-to-weight ratio and its ability to be programmed into a predetermined shape. Upon application, the alloy framework may provide a tunable and directional force (torque) superior to traditional metallic or polymeric strips (e.g., tunable by how much a user may pinch it, complicated by if the spring body is initially/delivered flat and bent/customized to shape by the user before application (e.g., force tunable via wire thickness, width, alloy composition, pre-set geometry, etc.)). A tunable mechanical force may be provided. Elastic properties and/or pre-set geometry of spring body 122 may allow for precise adjustment of the force and torque exerted by the assembly, thereby enabling customization for individual users. The reduced density of the selected alloy may result in a device mass that is lighter than, or at least comparable to, flat plastic devices, thereby improving user comfort during extended wear. For example, the use of advanced, low-density materials may result in a device mass of less than or equal to 1.2 grams, thereby enhancing comfort for prolonged use. The alloy may be bent and programmed to form paddle-shaped tips (e.g., at ends 122L and 122R), which may serve as mechanical leverage points for force transmission (see, e.g., paddle-shaped tips 222L" and 222R" of FIG. 4).

The memory element may be overmolded with a soft elastomeric polymer (e.g., component) that may occupy a central region of the spring subassembly and form a non-adhesive midline zone. This region may function as a mechanical leverage amplifier by creating a fulcrum elevation above skin, as well as a comfort interface between metal and skin (e.g., with or without bridge 136). The central non-adhesive void may allow the memory paddle tips (e.g., ends 122L/122R) to deflect further before damping, thereby increasing torque transfer efficiency (e.g., higher moment arm) compared to continuous adhesive devices. This also drastically reduces dermatologic trauma because adhesives may not be present in the nasal bridge area, which may be the highest shear stress region during removal. For example, at least a central portion of spring body 122 may be encapsulated in a cushion component 125 (e.g., a biocompatible, soft polymer material, such as silicone rubber or thermoplastic polyurethane). Such overmolding may provide a cushioning interface between the central portion of the device and the user's nasal bridge, reducing localized pressure and skin irritation, may create a separation between the device and the nasal bridge (e.g., the configuration of assembly 100 may ensure that a user's head UH (e.g., nasal dorsum ND) does not contact a central portion of assembly 100 (e.g., a central portion of assembly 100 between patches 132L and 132R) when assembly 100 is adhered to a user's head UH (e.g., to left lateral nasal wall LW and right lateral nasal wall RW of a user's nose)), effectively elevating the fulcrum and increasing the mechanical advantage at the paddle-shaped tips of the alloy, and/or form a pocket between the adhesive patches and the underlying alloy, thereby allowing for enhanced flexibility and more effective force transfer at the device extremities.

The patches (e.g., one or more of patches 112L, 12R, 132L, and 132R) may include one or more engineered radial slit patterns (e.g., slit(s) 114L, 114R, 134L, 134R, etc.), where such patterns may permit local bending micro articulation, which may permit assembly 100 to conform to wide variations in nasal curvature, nasal geometry, and dynamic movement during sleep without peeling. Dynamic flexibility may be provided. Slit patterns in the adhesive layers may accommodate skin movement, reduce shear forces, and/or minimize the risk of premature detachment from the user's face. Exterior subassembly 110 may be coupled to (e.g., laminated over) interior subassembly 130 to mechanically capture spring subassembly 120, where left interior patch interior surface 133L and right interior patch interior surface 133R may exclusively perform fixation to a user, thereby allowing mechanical, comfort, spring, and adhesive functions to be modularized and not coupled.

Assembly 100 may include two pressure-sensitive, double-sided adhesive patches (e.g., patches 132L and 132R) with radial slits to accommodate the complex contours of the nasal anatomy. An interior side of each patch may be intended to contact the skin and may be covered by a removable liner (e.g., subassembly 140), which may be peeled away immediately prior to application. The shape-memory alloy and overmolding (e.g., spring body 122 and component 125 and/or component 126) may be centrally positioned for ensuring precise alignment and force distribution. The assembly may also include two single-sided adhesive patches (e.g., patches 112L and 112R) with slits that may be laminated onto the external face of the double-sided patches, further securing the internal components. The slits in both adhesive layers may allow for multidirectional flexibility and conformability, maintaining secure adhesion during facial movements.

A hemispherical silicone bead (e.g., tactile element(s) 152L and 152R of subassembly 150) may be positioned directly above the tip center of each spring body end. Such a tactile element may provide a tactile landmark through patches 112L and 112R for a user's hand and/or may aid in coupling the ends of the spring body to their respective patch(es) (e.g., by providing additional surface area and/or covering a potentially sharp end of a spring body that might otherwise pose a threat of tearing a patch (e.g., a bead may surround a tip of a spring body end)). This bead may provide a tactile targeting landmark so the user can place the assembly with one hand, blind, in darkness, tactile only, and repeatedly achieve identical placement location night after night. This solves a very large compliance problem of other solutions that may have high positional variability. Such a bead may be composed of soft silicone and/or may be thermally bonded to an upper surface of the device, such as directly above the paddle-shaped tip of the alloy (e.g., an end 122L or end 122R of spring body 122). This bead may provide a tactile reference point, enabling the user to position the device consistently and accurately with a single hand, thereby improving application reliability and user experience.

In summary, the described nasal positioning device (e.g., assembly 100) may use advanced materials and a multi-component assembly to deliver superior mechanical performance, user comfort, and application consistency, representing a significant advancement over other nasal device solutions.

In some embodiments, a hydrogel reservoir pad may be placed within or on or otherwise provided by component 125 and/or component 126 and/or interior bridge 136 (e.g., with isotonic saline) for skin (e.g., slow release) humidification and comfort. This may provide slow release humidification and/or act as a cushion (e.g., a crosslinked polyvinyl alcohol ("PVA") or polyethylene glycol ("PEG") hydrogel loaded with isotonic saline and a humectant, such as with a size of 50-200 microliters).

In some embodiments, one or more aromatic polymer additives (e.g., menthol, chamomile, eucalyptus, xylitol, etc.) may be provided by any suitable portion(s) of assembly 100.

In some embodiments, different versions of assembly 100 may be provided with different respective spring force levels so a patient may be prescribed a particular type of assembly 100 based on nasal obstruction severity of the user and/or based on a particular geometry of the user's face, which may provide a customizable user experience.

In some embodiments, a fluorescent pigment additive may be provided by any suitable portion(s) of assembly 100 for detection and/or placement in low light environments.

In some embodiments, assembly 100 may be provided with a reduced width central region (e.g., bridge 116, spring body 122, component 125, component 126, and/or bridge 136) to further increase a torque concentration vector.

Therefore, when worn, the adhesive ends of the assembly may secure to the right and left nasal walls of a user. A spring body in the center may attempt to return to its natural programmed curvature. A non-adhesive elevated central region may prevent damping at midline, thereby amplifying torque toward the nasal valve. The result may be mechanical dilation that is directionally optimized normal to the airway lumen, producing more airflow while limiting user discomfort and associated skin injury when compared to other solutions. This may enable chronic nightly use users (e.g., including CPAP overlap therapy) who historically may not tolerate adhesive nasal strips due to skin injury risk, thereby materially expanding the available clinical population.

Therefore, in some embodiments, a nasal strip may be provided for opening the nasal passageways, the nasal strip may include features that include a curved nasal strip formed from a memory-shaped metal alloy material with paddle-shaped ends (e.g., body 122), the memory-shaped metal alloy material may be coated with soft plastic or rubber (e.g., component 125 or component 126), a central portion of the strip, which may be coated with soft plastic or rubber, does not have any adhesive, the strip may also include adhesive patches, where an interior surface of the internal portion having an adhesive coating that covers the interior surface of each end section of the internal portion of the nasal strip with the central portion not having an adhesive coating on its interior surface, the central portion having an increased thickness portion of the nasal strip when compared to the thickness of the end sections of the nasal strip, the increased thickness of the central portion creating an increased torque to be exerted outwardly on the sides of the nose when the end sections are adhesively attached to each side of the nose, this increased torque causing increased openings of the left and right nasal passage ways. In some embodiments, the central portion of the nasal strip may have a decreased width as compared to the width of the end sections of the nasal strip. In some embodiments, there is an adhesive covering on all interior surfaces of the interior portion of the nasal strip with the central portion of the nasal strip having a non-adhesive material covering the adhesive on that central portion of the nasal strip (e.g., surface 137 may include a non-adhesive covering an adhesive). In some embodiments, the length of the nasal strip is approximately 6 centimeters. In some embodiments, the width of the end sections of the nasal strip is approximately 2 centimeters. In some embodiments, the length of the central portion of the nasal strip is approximately 2.5 centimeters. In some embodiments, the memory shaped spring element includes a shape-memory metal alloy selected from Nitinol, beta titanium, copper-aluminum-nickel, or copper-zinc based memory alloys. In some embodiments, the memory shaped spring element is programmed to return to a predetermined curvature when unconstrained, providing torque normal to the nasal airway surface to increase nasal valve opening. In some embodiments, the memory shaped spring element is configured to deliver peak outward force depending on programming contour geometry. In some embodiments, the memory shaped element is encapsulated by a soft polymer overmolding selected from silicone rubber, TPE, TPU, medical grade elastomers, or blends thereof. In some embodiments, the overmolding (e.g., component 125) creates a pocket air-gap separation zone between the memory metal paddle tip and the adhesive patches, thereby increasing force amplification at the tip. In some embodiments, the adhesive end regions may include radial slit patterns configured to accommodate nasal curvature and micro motion of the skin during sleep. In some embodiments, the adhesive may include a double-sided pressure sensitive adhesive patch laminated to a single sided pressure sensitive adhesive patch. In some embodiments, the nasal strip may further include a soft silicone tactile bead positioned above the central portion of the memory alloy element to provide a physical targeting reference point during device placement. In some embodiments, the nasal strip may further include a hydrogel cushion pad (e.g., component 126) placed between the memory shaped alloy and the nasal skin, wherein the hydrogel reservoir may include isotonic buffered saline and/or a hydrogel that may include crosslinked PVA or PEG. In some embodiments, the nasal strip may further include an aromatic agent selected from menthol, chamomile, eucalyptus, xylitol, terpenoids, or mixtures thereof. In some embodiments, the nasal strip may further include fluorescent pigments incorporated into the polymer overmolding or adhesive layer. In some embodiments, the memory alloy may be manufactured in multiple predetermined levels of dilation force for selecting customized user experience.

As shown in FIGS. 2 and 2A-2J, a nasal dilation assembly 200 may include an exterior subassembly 210, a spring subassembly 220, and an interior subassembly 230. Spring subassembly 220 may include a spring body 222 that may extend between a left spring end 222L and a right spring end 222R. As shown in FIGS. 2 and 2A-2E, spring body 222 may be pre-configured to have a natural state that is flat (e.g., its natural state angle θn may be) 180°, although any other suitable natural state may be possible (e.g., as described with respect to assembly 100). Body 222 may be configured to spring back towards or otherwise attempt to return to its natural state from any suitable pinched state, where such a pinched state may be achieved when ends 222L and 222R are pinched towards each other through application of user pressure (e.g., in the directions of application arrows AL and AR, respectively). Spring body 222 may be made of any suitable material or combination of materials, any suitable density, and any suitable geometry (e.g., as described with respect to body 122 of assembly 100). Any suitable characteristics of body 222 (e.g., cross-sectional width, cross-sectional thickness, bend radius, etc.) may be customized to exert any desired force(s). In some embodiments, spring subassembly 220 may include any suitable cushion component 225, such as any suitable coating or overmold that may be provided about the entirety of spring body 222. For example, as shown, cushion component 225 may be provided about spring body 222 along an entirety of the length of spring body 222 between ends 222L and 222R, such that ends of cushion component 225 may cover ends 222L and 222R (see, e.g., FIG. 2A). In some embodiments, cushion component 225 may be a tubular cushion that may encapsulate the entire periphery (e.g., longitudinal periphery and end peripheries) of spring body 222 (e.g., for adhering to and encapsulating the entire structure of spring body 222). Cushion component 225 may be provided by any suitable material or combination of materials, including, but not limited to, silicone, foam, silicone foam, plastic, rubber, a biocompatible soft polymer overmold, silicone rubber, thermoplastic polyurethane/polyethylene, and/or the like. Cushion component 225 may be configured to provide any suitable cushion or comfort to a user's head UH (e.g., to the nasal dorsum ND extending along the front of a user's nose between its nasal root NR and its nasal tip NT) if the center of assembly 200 were to contact and push up against the front of the user's nose.

Interior subassembly 230 may include a left interior patch 232L and a right interior patch 232R. As shown, unlike interior subassembly 130, interior subassembly 230 might not also include a central interior bridge that may extend between patch 232L and patch 232R. Subassembly 230 (e.g., patch 232L and patch 232R) may be made of any suitable material or combination of materials, including, but not limited to, paper, coated paper, plastic or plastic films (e.g., PVC, PE, PP, PU, PET, etc.), nonwoven fabrics, woven fabrics, foam materials, latex, silicone, and/or the like. Similarly to interior patches 132L and 132R of assembly 100, left interior patch 232L of assembly 200 may provide a left interior patch exterior surface and an opposing left interior patch interior surface, while right interior patch 232R of assembly 200 may provide a right interior patch exterior surface and an opposing right interior patch interior surface. Each interior patch may be any suitable shape and any suitable size such that its interior patch exterior surface may contact a respective end region of spring subassembly 220 (e.g., ends 225L and 225R of cushion component 225) and such that its interior patch interior surface may contact a portion of a respective lateral nasal wall of a user's nose (e.g., left interior patch 232L may be configured to provide a left interior patch exterior surface for contacting a left end region 225L of cushion component 225 of subassembly 220 and a left exterior patch exterior surface for contacting a left lateral nasal wall LW of a user's nose, while right interior patch 232R may be configured to provide a right interior patch exterior surface for contacting a right end region 225R of cushion component 225 of subassembly 220 and a right exterior patch exterior surface for contacting a right lateral nasal wall RW of a user's nose). As with assembly 100, at least a portion of each one of the left interior patch interior surface and the right interior patch interior surface of assembly 200 may be provided by or with any suitable adhesive that may be configured to stick to the skin of a user (e.g., the skin of a user's lateral nasal wall (e.g., just above a nasal ala (e.g., lateral nasal wall RW just above nasal ala RA of nostril RN or lateral nasal wall LW just above nasal ala LA of nostril LN))) when assembly 200 is pinched onto a user's nose. As with assembly 100, at least a portion of each one of the left interior patch exterior surface and the right interior patch exterior surface of assembly 200 may be provided by or with any suitable adhesive that may be configured to stick to a portion of spring subassembly 220 and/or an opposing patch (e.g., a patch of any suitable exterior subassembly 210) when assembly 200 is fully assembled. One or each of left interior patch 232L and right interior patch 232R may include one or more slits formed therethrough (not shown), where each slit may enable the patch to more closely conform to the shape of the portion of the user's nose against which the patch may be pressed for adherence. One or more slits may be configured in any suitable manner or pattern, such as radially and/or angularly from a center of the patch to enable any suitable conformity with any suitable geometry of a user's face. It is to be understood that, in most embodiments, an exterior surface of cushion component 225 of subassembly 220 may be provided by or with any suitable non-adhesive material that may not stick to a user's skin if any contact with such skin is made (e.g., the front of a nasal dorsum), but instead the material of the exterior surface of cushion component 225 of subassembly 220 may be configured to provide any suitable non-adhering and comfortable surface for any possible interface with a user's skin. Such a non-adhering exterior surface of cushion component 225 of subassembly 220 may provide a non-sticky handling zone of a central portion of subassembly 220 (e.g., after any liner subassembly 240 has been removed) that may enable simplified placement, alignment, and application of assembly 200 onto a user's face without that non-sticky handling zone sticking to the user's face and/or fingers. Moreover, such mechanical decoupling due to such a non-adhering exterior surface of cushion component 225 of subassembly 220 may reduce or prevent damping of spring force, thereby enabling more efficient force transmission during assembly use, and/or thereby reducing shear stress during assembly removal.

Assembly 200 may also include a liner subassembly 240 that may include a left liner patch 242L and a right liner patch 242R, and which may be similar to liner subassembly 140 of assembly 100. Each liner patch of liner subassembly 240 may be any suitable shape and any suitable size such that its liner patch exterior surface may contact and cover at least a portion if not all of an opposing exterior patch exterior surface of subassembly 230 to protect the adhesive portion of that exterior patch exterior surface until it is ready for use.

In some embodiments, spring subassembly 220 may be coupled to interior subassembly 230 using any suitable adhesive that may be provided by any suitable exterior surface(s) of interior subassembly 230 (e.g., any suitable adhesive of the left interior patch exterior surface and/or any suitable adhesive of the right interior patch exterior surface). Additionally or alternatively, spring subassembly 220 may be coupled to interior subassembly 230 using any suitable exterior subassembly 210, which may be coupled to interior subassembly 230 for sandwiching at least a portion of spring subassembly 220 therebetween. For example, exterior subassembly 210 may include a left exterior patch 212L and a right exterior patch 212R. As shown, exterior subassembly 210 may not include a central exterior bridge like that of subassembly 110 extend between its patches. Patches 212L and 212R of subassembly 210 may be similar to patches 112L and 112R of subassembly 110. Therefore, any suitable adhesive provided along any suitable interior portion(s) of exterior subassembly 210 and/or any suitable adhesive provided along any suitable exterior portion(s) of interior subassembly 230 may be used to couple interior subassembly 230 to exterior subassembly 210 while retaining at least a portion of spring subassembly 220 therebetween. In some embodiments, in addition to or as an alternative to cushion component 225 that may be provided about at least a central region of spring body 222, any suitable cushion element(s) (e.g., similar to element(s) 126 of assembly 100) may be positioned between spring body 222 and cushion component 225 (not shown). One or each of left exterior patch 212L and right exterior patch 212R may include one or more slits formed therethrough (not shown), where each exterior subassembly slit may align with each interior subassembly slit such that the aligned slits may enable the aligned interior/exterior patches to more closely conform to the shape of the portion of the user's nose against which the interior patch may be pressed for adherence. One or more slits may be configured in any suitable manner or pattern, such as radially and/or angularly from a center of the patch to enable any suitable conformity with any suitable geometry of a user's face.

Assembly 200 may include any suitable tactile subassembly 250 that may be provided to enable a user to locate and manipulate appropriate portions of assembly 200 for deforming spring subassembly 220 from its natural state to a pinched state for coupling to a user's face. For example, subassembly 250 may include a left tactile element 252L and/or a right tactile element 252R. In some embodiments, left tactile element 252L may be sandwiched between exterior patch 212L and spring body end 222L, and/or right tactile element 252R may be sandwiched between exterior patch 212R and spring body end 222R, such that when assembly 200 is fully assembled, a user may be able to feel a tactile element through an exterior patch, which may enable the user to locate an appropriate portion of spring body 222 for reconfiguring spring body 222 from its natural state to a pinched state. For example, in some embodiments, each one of tactile elements 252L and 252R may be provided as a soft silicon bead (e.g., half-sphere bead) or any other suitable soft material (e.g., a material that may be provided as a liquid during assembly of assembly 200 and that may then set to a solid at room temperature), where each tactile element may be configured to cover an end of cushion component 225 and create a protrusion (e.g., a bump) at a portion of a patch of exterior subassembly 210 for enabling easy user handling. In some embodiments, where assembly 200 may not include an exterior subassembly 210, a tactile element may be contacted directly by a user during handling and coupling of assembly 200 to a user's face (e.g., a tactile component may be coupled to a patch 232 and contacted by a user. In some embodiments, a tactile element may be configured to at least partially couple an end region of cushion component 225 to a patch of interior subassembly 230 and/or to a patch of exterior subassembly 210. When assembly 200 has been fully assembled and ready for use, a user may use right tactile element 252R to enable their right thumb to locate end 225R and press with any suitable user force on element 252R and end 225R in the direction of arrow AR (e.g., at a bump caused by element 252R), and user may use left tactile element 252L to enable their right index finger to locate end 255L and press with any suitable force on element 252L and end 255L in the direction of arrow AL (e.g., at a bump caused by element 252L) when attempting to secure assembly 200 to the user's nose in order to achieve a pinched state (it is to be noted that elements 252L and 252R may not be shown in FIGS. 2B-2J).

Figures 2, 2A, 2B:
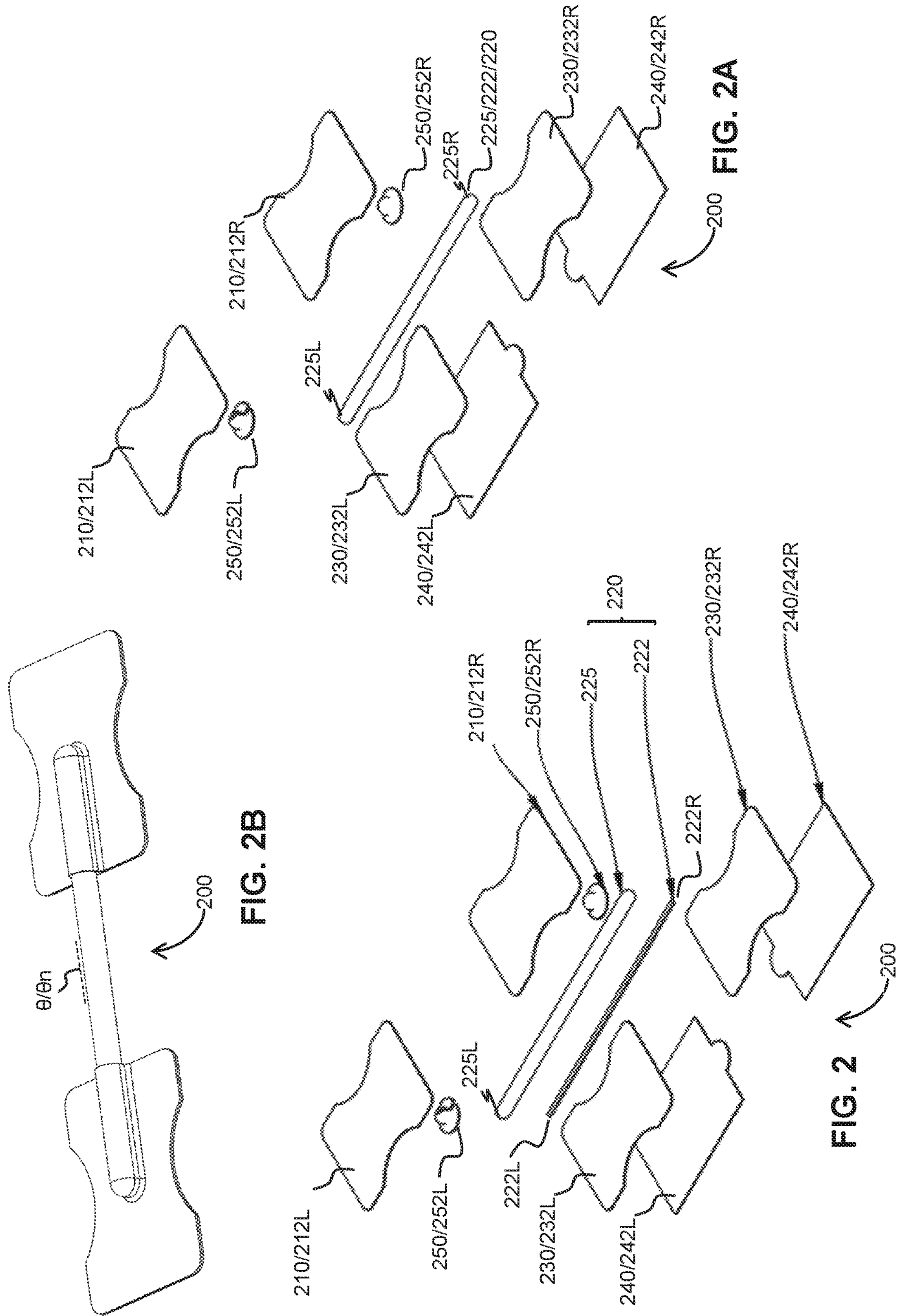
FIG. 2 illustrates an exploded perspective view of another nasal dilation assembly in a natural state, according to one or more embodiments of the disclosure.
FIG. 2A illustrates a partially exploded perspective view of the nasal dilation assembly of FIG. 2 in its natural state, according to one or more embodiments of the disclosure.
FIG. 2B illustrates another perspective view of the nasal dilation assembly of FIGS. 2 and 2A in its natural state, according to one or more embodiments of the disclosure.
Figures 2C, 2D, 2E:
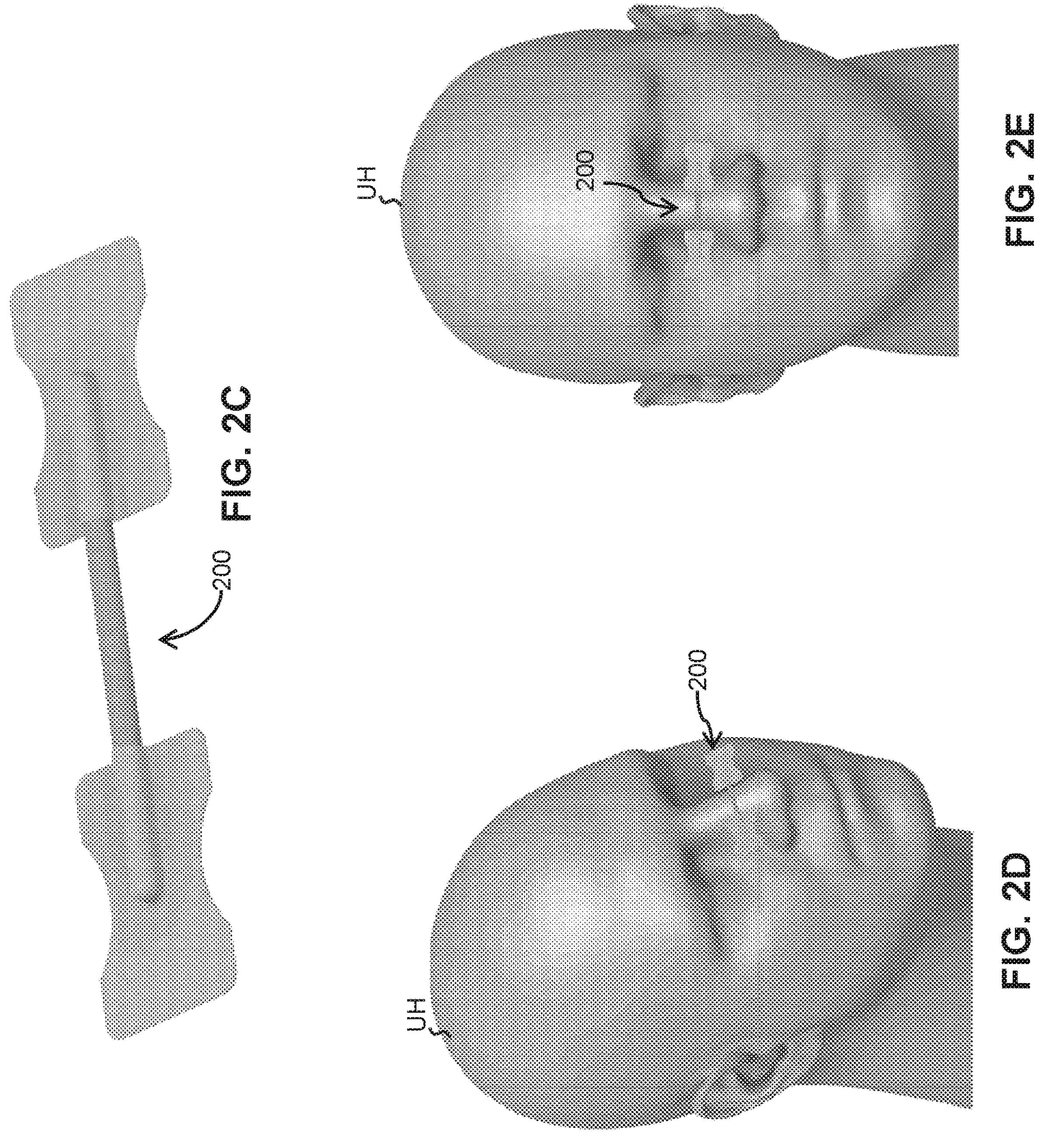
FIG. 2C illustrates another perspective view of the nasal dilation assembly of FIGS. 2, 2A, and 2B in its natural state, according to one or more embodiments of the disclosure.
FIG. 2D illustrates another perspective view of the nasal dilation assembly of FIGS. 2 and 2A-2C in its natural state adjacent the user's head of FIGS. 1A-1C, according to one or more embodiments of the disclosure.
FIG. 2E illustrates a front view of the nasal dilation assembly of FIGS. 2 and 2A-2D in its natural state adjacent the user's head of FIGS. 1A-1C and 2D, according to one or more embodiments of the disclosure.
Figures 2F, 2G, 2H:
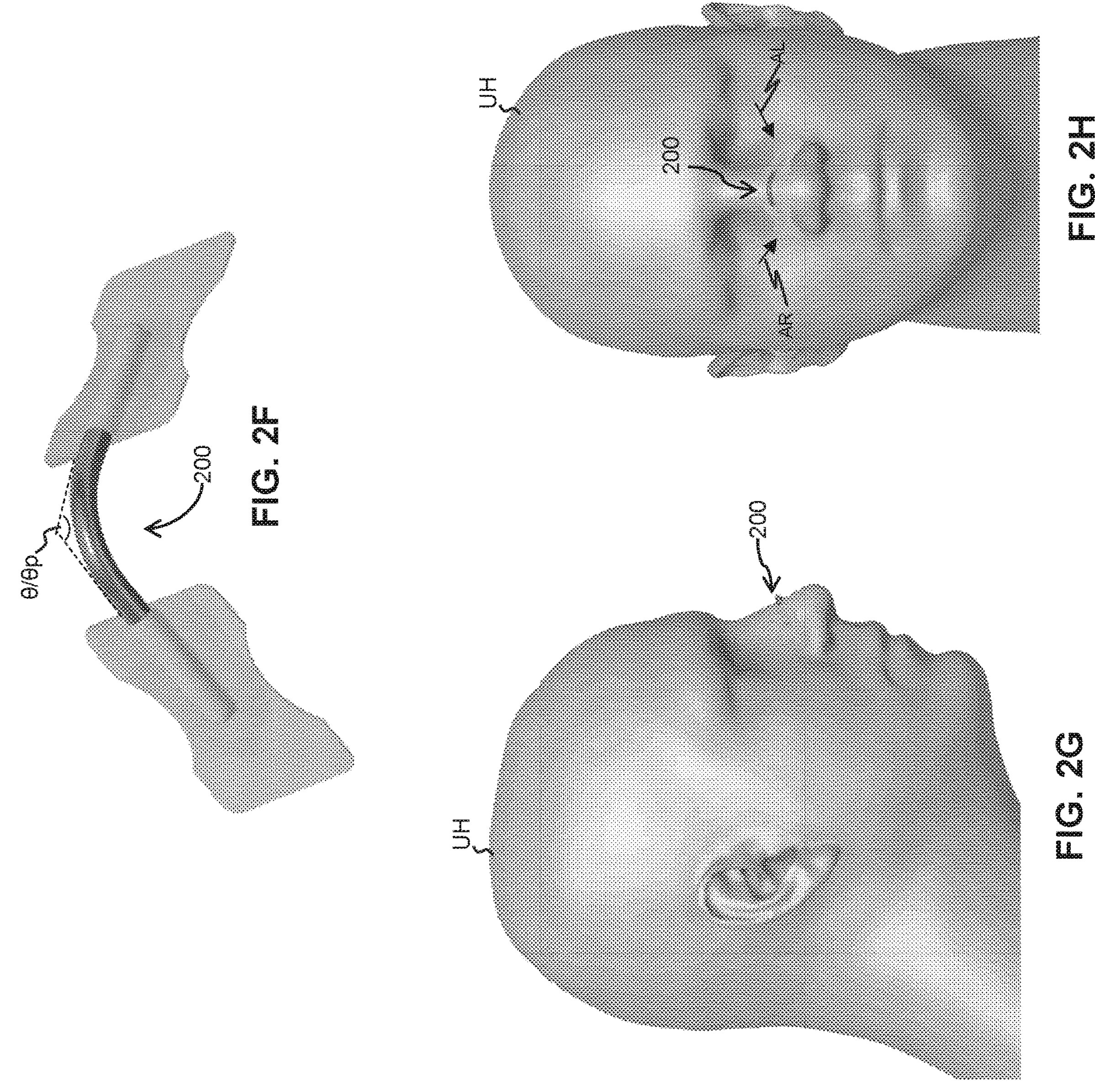
FIG. 2F illustrates another perspective view of the nasal dilation assembly of FIGS. 2 and 2A-2E in its pinched state, according to one or more embodiments of the disclosure.
FIG. 2G illustrates a side view of the nasal dilation assembly of FIGS. 2 and 2A-2F in its pinched state adjacent the user's head of FIGS. 1A-1C, 2D, and 2E, according to one or more embodiments of the disclosure.
FIG. 2H illustrates a front view of the nasal dilation assembly of FIGS. 2 and 2A-2G in its pinched state adjacent the user's head of FIGS. 1A-1C, 2D, 2E, and 2G, according to one or more embodiments of the disclosure.
Figure 2J:
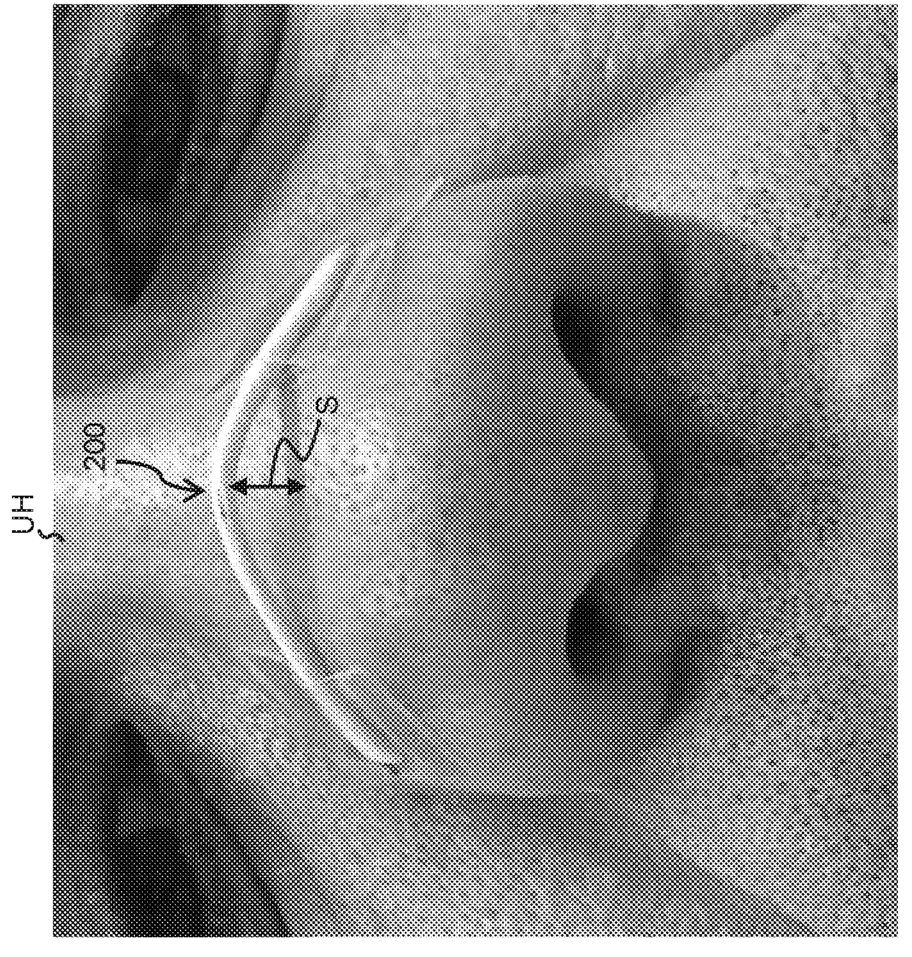
FIG. 2J illustrates another front view of the nasal dilation assembly of FIGS. 2 and 2A-2I in its pinched state adjacent the user's head of FIGS. 1A-1C, 2D, 2E, 2G, 2H, and 2I, according to one or more embodiments of the disclosure.
Figure 2I:
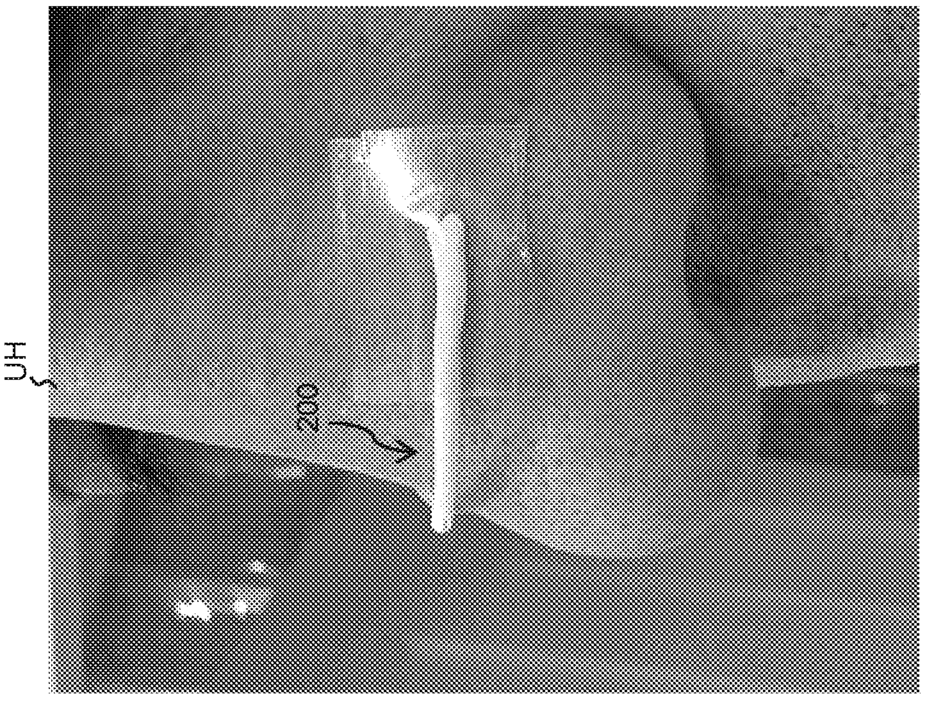
FIG. 2I illustrates another side view of the nasal dilation assembly of FIGS. 2 and 2A-2H in its pinched state adjacent the user's head of FIGS. 1A-1C, 2D, 2E, 2G, and 2H, according to one or more embodiments of the disclosure.

As shown, once assembled and ready for use (e.g., once any liner subassembly 240 has been removed), assembly 200 may be moved in the direction of arrow A towards the user's face such that the interior surfaces of interior subassembly 230 may be positioned adjacent to but not contacting the user's face (see, e.g., the position of FIGS. 2D and 2E) and then assembly 200 (e.g., spring subassembly 220) may be reconfigured from its natural state to a pinched state, such as by a user simultaneously applying a pinch force in the direction of arrow AR on or near feature 252R/end 225R and a pinch force in the direction of arrow AL on or near feature 252L/end 225L, whereby at least a portion of the interior patch interior surface of left interior patch 232L of interior subassembly 230 may contact and stick to left lateral nasal wall LW of the user's nose and at least a portion of the interior patch interior surface of right interior patch 232R of interior subassembly 230 may contact and stick to right lateral nasal wall LR of the user's nose, and whereby a central portion of subassembly 220 (e.g., a central portion of cushion component 225) may contact a portion of nasal dorsum ND of the user's nose or may not contact a portion of nasal dorsum ND of the user's nose (see, e.g., space S of FIG. 2J). Then, once the user terminates such a pinch force on assembly 200, spring assembly 220 may attempt to reconfigure itself from the pinched state back to its natural state. However, due to the adhesion of assembly 200 to the user's face (e.g., adhesion of the interior patch interior surface of left interior patch 232L of interior subassembly 230 to left lateral nasal wall LW of the user's nose and adhesion of the interior patch interior surface of right interior patch 232R of interior subassembly 230 to right lateral nasal wall LR of the user's nose), such a reconfiguration attempt may be limited. For example, while the pinching may reduce natural state angle θ of spring subassembly 220 from 100% of natural state angle θ in the natural state of assembly 200 of FIGS. 2 and 2A-2E (or the preformed natural state as customized by the user (e.g., if the spring subassembly may be delivered to an end user flat or any other suitable delivered natural state and then reconfigured to a user customized natural state by a user before use)) (e.g., natural state angle θn (e.g., as delivered or as preformed as customized by the user after delivery)) to any suitable pinched reduced percentage of angle θ (e.g., 30%-90% or 60% or any other suitable percentage of angle θn (i.e., a pinched reduced angle θp)) in the pinched state of assembly 200 of FIGS. 2F-2H, the termination of a pinching force but addition of an adhesion force on assembly 200 may enable an increase of the angle of spring subassembly 220 from its pinched reduced percentage of angle θn in its pinched state to any suitable adhered reduced percentage of angle θ (e.g., 70%-80% or 75% or any other suitable percentage of angle θn (i.e., an adhered interim angle θi)) in its adhered state (e.g., where an adhered interim angle θi may be greater than pinched reduced angle θp but less than natural state angle θn). This reconfiguration of assembly 200 from the pinched state and pinched reduced angle θp to the adhered state and adhered interim angle θi that may be any suitable angle greater than pinched reduced angle θp while interior patches 232L and 232R remain adhered to lateral nasal walls LW and RW may enable assembly 200 to exert outward mechanical forces on the user's nose (e.g., expansion forces that may be in directions opposite to the directions of arrows AL and AR) to enlarge the nasal valve region of the user's nose (e.g., the geometry and configuration of spring body 222 along with the adhesion properties of interior subassembly 230 may provide two enhanced torque vectors, each of which may be normal to a respective an airway lumen and may increase an airway opening).

Therefore, assembly 200 may provide an improved nasal strip design that increases the mechanical efficiency of airway dilation while reducing the dermatologic and handling limitations of various prior designs. Improvements may include increased mechanical leverage without increased user discomfort, improved directionality of opening force, simplified handling during application, and a meaningful reduction in the total adhesive contact area with the skin. A device capable of achieving these improvements while remaining non-invasive and externally applied represents a significant advancement in nasal dilation technology. Assembly 200 may incorporate features that make the assembly easier to handle and position on the nose for simplifying its application, such as with a non-adhering exterior surface of cushion component 225 and/or with tactile subassembly 250 and/or with any slits of any patches. Assembly 200 may minimize the amount of skin exposed to adhesive to help prevent irritation and make the assembly suitable for a wider range of users, such as with a non-adhering exterior surface of cushion component 225. Assembly may increase the force or leverage applied to gently open the nasal airway to improve airflow (e.g., increased mechanical leverage without increased user discomfort), which may be enabled by a spring body made of a robust material (e.g., a metal alloy) and configured with a curved natural state.

Figures 3, 3A, 3B:
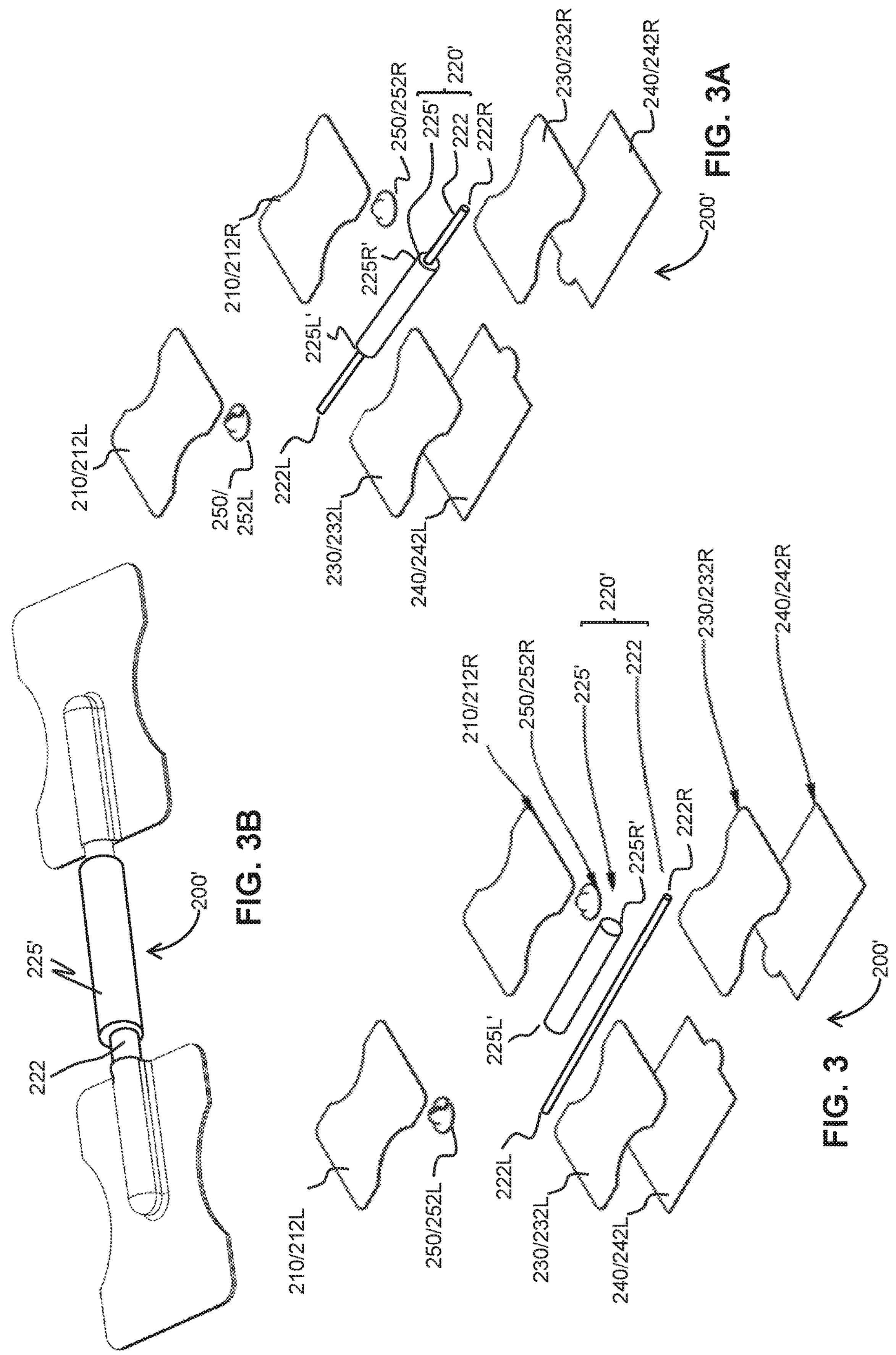
FIG. 3 illustrates an exploded perspective view of yet another nasal dilation assembly in a natural state, according to one or more embodiments of the disclosure.
FIG. 3A illustrates a partially exploded perspective view of the nasal dilation assembly of FIG. 3 in its natural state, according to one or more embodiments of the disclosure.
FIG. 3B illustrates another perspective view of the nasal dilation assembly of FIGS. 3 and 3A in its natural state, according to one or more embodiments of the disclosure.

As shown in FIGS. 3, 3A, and 3B, another assembly 200' may be provided, which may be substantially identical to assembly 200, except that assembly 200' may include spring subassembly 220'. Spring subassembly 220' may include spring body 222 of assembly 220, but may include a cushion component 225' that may be shorter than cushion component 225. For example, as shown, spring subassembly 220' may include any suitable cushion component 225', such as any suitable coating or overmold that may be provided about any suitable portion but not the entire length of spring body 222. For example, as shown, cushion component 225' may be provided about spring body 222 along only a portion of the length of spring body 222 between ends 222L and 222R of spring body 221, such that ends 225L' and 225R' of cushion component 225' may not cover ends 222L and 222R of spring body 221 (see, e.g., FIG. 3A). In some embodiments, cushion component 225' may be a tubular cushion that may encapsulate a portion of (e.g., a central portion of) the longitudinal periphery of spring body 222 but neither end periphery of spring body 222 (e.g., cushion component 225' may extend about spring body 222 along only a portion of the length between ends 222L and 222R, but not including the ends of spring body 222 and/or but not including the end portions of spring body 222 that may be held between respective patches 212 and 232). Cushion component 225' may be provided by any suitable material or combination of materials, including, but not limited to, silicone, foam, silicone foam, plastic, rubber, a biocompatible soft polymer overmold, silicone rubber, thermoplastic polyurethane/polyethylene, and/or the like. Cushion component 225' may be configured to provide any suitable cushion or comfort to a user's head UH (e.g., to the nasal dorsum ND extending along the front of a user's nose between its nasal root NR and its nasal tip NT) if the center of assembly 200' were to contact and push up against the front of the user's nose. Therefore, ends 225L' and 225R' of cushion component 225' may be exposed when assembly 200' is fully formed (see, e.g., FIG. 3B), whereby ends 222L and 222R of spring body 222 may be directly held by patches 212/232 and/or tactile elements 252L/252R.

Figure 4:
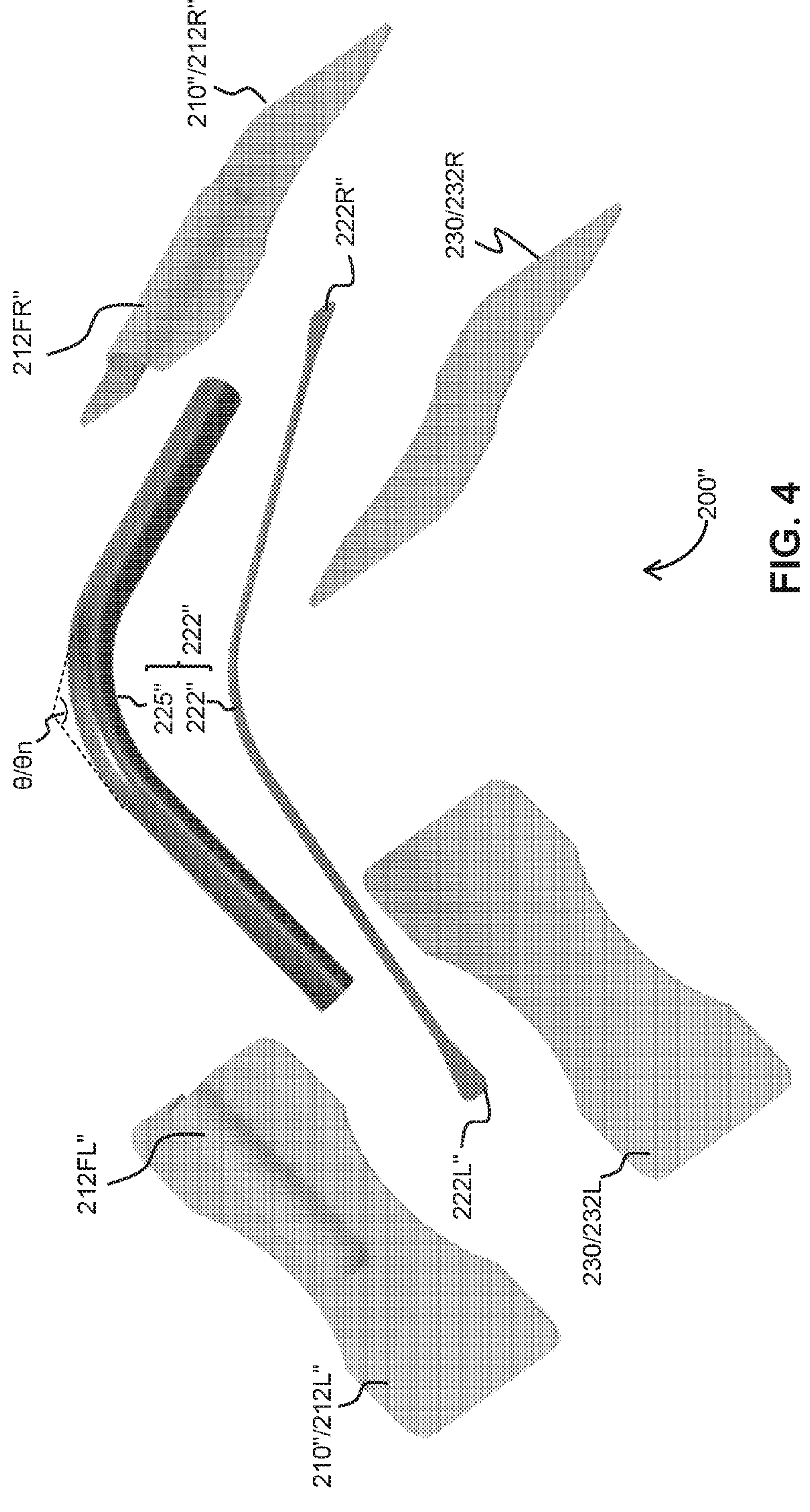
FIG. 4 illustrates an exploded perspective view of still yet another nasal dilation assembly in a natural state, according to one or more embodiments of the disclosure.

As shown in FIG. 4, another assembly 200" may be provided, which may be substantially identical to assembly 200 or assembly 200', except that assembly 200" may include spring subassembly 220" and a subassembly 210". Spring subassembly 220" may include a spring body 222" that may extend between ends 222L" and 222R", which may be flattened or otherwise formed to provide any suitable paddle-shaped tips, which may serve as mechanical leverage points for force transmission and/or adhesion to patch(es). Subassembly 210" may be similar to subassembly 210 of assembly 200 and/or assembly 200', except that patches 212L" and 212R' may respectively include spring receiving features 212FL" and 212FR" in their natural states, which may be configured to help hold spring subassembly 220" to subassembly 210" and subassembly 230. In some embodiments, as shown in FIG. 4, spring receiving features 212FL" and 212FR" may be preformed impressions in the overlying adhesive. However, in other embodiments, such features may be formed by wrapping malleable top patches about ends of the spring body when coupling the various patches to the spring body (see, e.g., FIGS. 2-3B). Unlike as may be shown by the natural state of assembly 200 in FIGS. 2-2B and the natural state of assembly 200' in FIGS. 3-3B, the natural state angle θn of subassembly 222" (e.g., spring component 222" and cushion component 225") of FIG. 4 might not be 180° (e.g., flat), but might be some other preformed angle or some angle that may be customized by the user after receipt but prior to use. In some embodiments, this natural state angle may be created by the user (e.g., they may bend assembly 200" once assembled to customize this angle of curvature to provide a customized natural state angle prior to application on their nose). Therefore, an end user may bend the assembly (e.g., the assembly's spring body) to customize this angle to curve around their own unique nasal anatomy. In some embodiments, the assembly's spring body may be provided to the end user without a prebent natural state angle θn (e.g., the spring body may be shipped to an end user with an angle of 180° or otherwise). Some shape memory alloys (e.g., nitinol) may use a heat treatment that may allow the metal to achieve a bent angle θ. This shape may be intrinsic to the assembly's spring body that has been heat treated. In some embodiments, an assembly's spring body may be any suitable material (e.g., beta titanium) that may be different and can be bent by a user into a unique shape at room temperature. Such a spring body may still retain springiness after being bent into this shape (e.g., cold forming). As such, the shape may not be pre-programmed into the assembly's spring body. After a user bends the assembly's spring body to fit their own unique nasal anatomy, the bent angle may be set. The amount of recoil force created may also be dictated by how much the assembly's spring body is pinched together during application. If the assembly's spring body is pinched a lot before application, there may be more force created. Therefore, the adhesive on either side of the nose may lie more medially (e.g., closer to midline) than if the assembly's spring body was not pinched a lot (e.g., adhesive on either side of the nose may be more laterally placed). With a lot of pinch, the center fulcrum may also be elevated away from the midline nasal dorsum skin. Therefore, there may be two points of customization here. This is what may make this assembly's spring body special. Benefits of the unique angle θ may be that it is unique to a user's nose. Also, raising the fulcrum away from the nasal dorsum skin may prevent skin irritation.

In some embodiments, there is provided an external nasal dilator assembly including a spring subassembly that includes a spring body including a spring body central portion extending between a first spring body end and a second spring body end, and a cushion component about the spring body along at least a portion of the spring body central portion, a first adhesive patch coupled to a first spring subassembly end of the spring subassembly, and a second adhesive patch coupled to a second spring subassembly end of the spring subassembly. In some specific embodiments, the first adhesive patch is configured to adhere to a first lateral nasal wall of a user when the assembly is applied to the user and the second adhesive patch is configured to adhere to a second lateral nasal wall of the user when the assembly is applied to the user, and, in further embodiments, the assembly exerts outward mechanical force on the first and second lateral nasal walls to enlarge a nasal valve region of the user when the assembly is applied to the user. In some specific embodiments, the spring body is a shape-memory alloy wire. In some specific embodiments, the spring body is one of plastic or metal. In some specific embodiments, the cushion component is a coating for the spring body. In some specific embodiments, the cushion component is an overmold for the spring body. In some specific embodiments, the cushion component is at least one of the following: silicone, foam, plastic, rubber, or thermoplastic. In some specific embodiments, the cushion component encapsulates the spring body. In some specific embodiments, an exterior surface of the cushion component is a non-adhesive. In some specific embodiments, the cushion component is a resilient tubular cushion with a non-adhesive exterior surface that covers the entire spring body. In some specific embodiments, the assembly also includes a tactile positioning element coupled to the first adhesive patch, where, in some further embodiments, another tactile positioning element is coupled to the second adhesive patch, and/or the tactile positioning element provides a tactile indication detectable by the user to facilitate positioning of the assembly when the assembly is being applied to the user, and/or the tactile positioning element includes a soft silicon bead. In some specific embodiments, a natural state of the spring subassembly is configured to be adjustable by the user prior to application of the assembly. In some specific embodiments, the assembly also includes an interior subsystem including a central interior bridge coupling the first and second adhesive patches, and, in some further embodiments, the assembly also includes an exterior subsystem including a central exterior bridge extending between a first exterior patch and a second exterior patch, wherein the interior subsystem is adhered to the second subsystem about at least a portion of the spring subassembly, and/or an exterior subsystem including a central exterior bridge extending between a first exterior patch and a second exterior patch, wherein the interior subsystem is adhered to the second subsystem about at least a portion of the cushion component. In some specific embodiments, the spring body is programmed to return to a predetermined curvature when unconstrained. In some specific embodiments, the first adhesive patch includes a slit configured to accommodate nasal curvature.

Therefore, external nasal dilators and methods for using and manufacturing the same are provided. An external nasal dilator assembly may include a spring element (e.g., a shape-memory alloy wire) having first and second ends and a central portion. A resilient tubular cushion may encapsulate at least a portion of the spring element. First and second adhesive patches may be coupled to respective ends of the spring element and configured to adhere to lateral nasal walls of a user. At least one tactile positioning element may be coupled to at least one adhesive patch to facilitate positioning of the assembly during application. The spring element may be flat for user-customized bending or preformed to a curved state. The cushion may encapsulate the full length or only a central portion of the spring element. A non-adhesive central zone may be provided between the adhesive patches. When applied, the assembly may exert outward mechanical force on the lateral nasal walls to enlarge the nasal valve region.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. The term "and/or" as used herein refers to and encompasses any and all possible combinations of one or more of the associated listed items. As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" may each refer to only A, only B, or only C; any combination of A, B, and C; and/or at least one of each of A, B, and C. The terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. When used in the claims, the term "or" is used as an inclusive or and not as an exclusive or. For example, the phrase "at least one of x, y, or z" means any one of x, y, and z, as well as any combination thereof.

As used herein, the term “or” can be construed in either an inclusive or exclusive sense. Moreover, plural instances can be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and can fall within a scope of various implementations of the present disclosure. In general, structures and functionality presented as separate resources in the example configurations can be implemented as a combined structure or resource. Similarly, structures and functionality presented as a single resource can be implemented as separate resources. These and other variations, modifications, additions, and improvements fall within a scope of implementations of the present disclosure as represented by the appended claims. The specification and drawings are, accordingly, to be regarded in an illustrative rather than a restrictive sense.

The term “if” is, optionally, construed to mean “when” or “upon” or “in response to determining” or “in response to detecting,” depending on the context. Similarly, the phrase “if it is determined” or “if [a stated condition or event] is detected” is, optionally, construed to mean “upon determining” or “in response to determining” or “upon detecting [the stated condition or event]” or “in response to detecting [the stated condition or event],” depending on the context.

As may be used herein, the terms “component,” “module,” and “system,” are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server may be a component. One or more components may reside within a process and/or thread of execution and a component may be localized on one computer and/or distributed between two or more computers.

The predicate words “configured to,” “operable to,” “operative to,” do not imply any particular tangible or intangible modification of a subject, but, rather, are intended to be used interchangeably.

As used herein, the term “based on” may be used to describe one or more factors that may affect a determination. However, this term does not exclude the possibility that additional factors may affect the determination. For example, a determination may be solely based on specified factors or based on the specified factors as well as other, unspecified factors. The phrase “determine A based on B” specifies that B is a factor that is used to determine A or that affects the determination of A. However, this phrase does not exclude that the determination of A may also be based on some other factor, such as C. This phrase is also intended to cover an embodiment in which A may be determined based solely on B. As used herein, the phrase “based on” may be synonymous with the phrase “based at least in part on.”

As used herein, the phrase “in response to” may be used to describe one or more factors that trigger an effect. This phrase does not exclude the possibility that additional factors may affect or otherwise trigger the effect. For example, an effect may be solely in response to those factors, or may be in response to the specified factors as well as other, unspecified factors. The phrase “perform A in response to B” specifies that B is a factor that triggers the performance of A. However, this phrase does not foreclose that performing A may also be in response to some other factor, such as C. This phrase is also intended to cover an embodiment in which A is performed solely in response to B.

Phrases such as an aspect, the aspect, another aspect, some aspects, one or more aspects, an implementation, the implementation, another implementation, some implementations, one or more implementations, an embodiment, the embodiment, another embodiment, some implementations, one or more implementations, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

The word “exemplary” is used herein to mean “serving as an example, instance, or illustration”. Any embodiment described herein as “exemplary” or as an “example” or as an “embodiment” is not necessarily to be construed as preferred or advantageous over other implementations. Furthermore, to the extent that the term “include,” “have,” or the like is used in the description or the claims, such term is intended to be inclusive in a manner similar to the term “comprise” as “comprise” is interpreted when employed as a transitional word in a claim.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase “means for” or, in the case of a method claim, the element is recited using the phrase “step for”.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean “one and only one” unless specifically so stated, but rather “one or more”. Unless specifically stated otherwise, the term “some” refers to one or more. Pronouns in the masculine (e.g., his) include the feminine and neuter/neutral gender (e.g., her and its and they) and vice versa. Headings and subheadings, if any, are used for convenience only and do not limit the subject disclosure.

While there have been described external nasal dilators and methods for using and manufacturing the same, many changes may be made therein without departing from the spirit and scope of the subject matter described herein in any way. Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. It is also to be understood that various directional and orientational terms, such as "left" and "right," "up" and "down," "front" and "back" and "rear," "top" and "bottom" and "side," "above" and "below," "length" and "width" and "thickness" and "diameter" and "cross-section" and "longitudinal," "X-" and "Y-" and "Z-," "roll" and "pitch" and "yaw," "clockwise" and "counter-clockwise," and/or the like, may be used herein only for convenience, and that no fixed or absolute directional or orientational limitations are intended by the use of these terms. For example, the components of the apparatus can have any desired orientation. If reoriented, different directional or orientational terms may need to be used in their description, but that will not alter their fundamental nature as within the scope and spirit of the disclosure.

Therefore, those skilled in the art will appreciate that the concepts of the disclosure can be practiced by other than the described embodiments, which are presented for purposes of illustration rather than of limitation.

What is claimed is:

1. An external nasal dilator assembly comprising:

a spring subassembly comprising:

a spring body comprising a spring body central portion extending between a first spring body end and a second spring body end; and a cushion component about the spring body along at least a portion of the spring body central portion;

a first adhesive patch coupled to a first spring subassembly end of the spring subassembly; and a second adhesive patch coupled to a second spring subassembly end of the spring subassembly;

wherein the cushion component is a resilient tubular cushion with a non-adhesive exterior surface that covers the entire spring body.

2. The assembly of claim 1, wherein:

the first adhesive patch is configured to adhere to a first lateral nasal wall of a user when the assembly is applied to the user; and the second adhesive patch is configured to adhere to a second lateral nasal wall of the user when the assembly is applied to the user.

3. The assembly of claim 2, wherein the assembly exerts outward mechanical force on the first and second lateral nasal walls to enlarge a nasal valve region of the user when the assembly is applied to the user.

4. The assembly of claim 1, wherein the spring body is one of plastic or metal.

5. The assembly of claim 1, wherein the cushion component is a coating for the spring body.

6. The assembly of claim 1, wherein the cushion component is an overmold for the spring body.

7. The assembly of claim 1, wherein the cushion component is at least one of the following: silicone, foam, plastic, rubber, or thermoplastic.

8. The assembly of claim 1, wherein the cushion component encapsulates the spring body.

9. The assembly of claim 1, further comprising a tactile positioning element coupled to the first adhesive patch.

10. The assembly of claim 9, further comprising another tactile positioning element coupled to the second adhesive patch.

11. The assembly of claim 9, wherein the tactile positioning element provides a tactile indication detectable by the user to facilitate positioning of the assembly when the assembly is being applied to the user.

12. The assembly of claim 9, wherein the tactile positioning element comprises a soft silicon bead.

13. The assembly of claim 1, wherein a natural state of the spring subassembly is configured to be adjustable by the user prior to application of the assembly.

14. The assembly of claim 1, further comprising an interior subsystem comprising a central interior bridge coupling the first and second adhesive patches.

15. The assembly of claim 14, further comprising an exterior subsystem comprising a central exterior bridge extending between a first exterior patch and a second exterior patch, wherein the interior subsystem is adhered to the exterior subsystem about at least a portion of the spring subassembly.

16. The assembly of claim 14, further comprising an exterior subsystem comprising a central exterior bridge extending between a first exterior patch and a second exterior patch, wherein the interior subsystem is adhered to the exterior subsystem about at least a portion of the cushion component.

17. The assembly of claim 1, wherein the spring body is programmed to return to a predetermined curvature when unconstrained.

18. The assembly of claim 1, wherein the first adhesive patch comprises a slit configured to accommodate nasal curvature.

19. The assembly of claim 1, wherein the spring body comprises a shape-memory alloy wire.

* * * * *